(12) United States Patent
Goodman et al.

(10) Patent No.: US 7,550,310 B2
(45) Date of Patent: Jun. 23, 2009

(54) TECHNIQUES AND SYSTEMS FOR ANALYTE DETECTION

(75) Inventors: Rodney M. Goodman, Altadena, CA (US); Nathan S. Lewis, La Canada, CA (US); Robert H. Grubbs, So. Pasadena, CA (US); Jeffery Dickson, Pasadena, CA (US); Vincent F. Koosh, Pasadena, CA (US); Richard S. Payne, La Jolla, CA (US)

(73) Assignee: California Institute of Technology, Pasadena, CA (US)

( * ) Notice: Subject to any disclaimer, the term of this patent is extended or adjusted under 35 U.S.C. 154(b) by 136 days.

(21) Appl. No.: 11/439,136

(22) Filed: May 24, 2006

(65) Prior Publication Data
US 2006/0208254 A1    Sep. 21, 2006

Related U.S. Application Data

(60) Division of application No. 10/280,795, filed on Oct. 24, 2002, now Pat. No. 7,061,061, which is a division of application No. 09/276,988, filed on Mar. 26, 1999, now Pat. No. 6,495,892, which is a continuation of application No. PCT/US98/16527, filed on Aug. 7, 1998, and a continuation of application No. 09/130,775, filed on Aug. 7, 1998, now abandoned.

(60) Provisional application No. 60/092,707, filed on Jul. 14, 1998, provisional application No. 60/081,182, filed on Apr. 9, 1998, provisional application No. 60/055,071, filed on Aug. 8, 1997.

(51) Int. Cl.
*H01L 21/00* (2006.01)
*H01L 21/4763* (2006.01)

(52) U.S. Cl. ......................... 438/49; 438/631

(58) Field of Classification Search ......... 257/252–253, 257/414; 438/1, 6, 49, 99, 626, 631–634, 438/645–646, 648–651, 800, 939
See application file for complete search history.

(56) References Cited

U.S. PATENT DOCUMENTS 3,964,083 A    6/1976    Lohstroh (Continued)

FOREIGN PATENT DOCUMENTS

EP    0774662    11/1996

(Continued)

OTHER PUBLICATIONS

Diorio et al., "A floating-gate MOS learning array with locally computed weight updates" IEEE Transactions on Electronic Devices 44:2281-2289 (1997).

(Continued)

*Primary Examiner*—Douglas M Menz
*Assistant Examiner*—Matthew W Such
(74) *Attorney, Agent, or Firm*—Foley & Lardner LLP

(57) ABSTRACT

Techniques are used to detect and identify analytes. Techniques are used to fabricate and manufacture sensors to detect analytes. An analyte (810) is sensed by sensors (820) that output electrical signals in response to the analyte. The electrical signals may be preprocessed (830) by filtering and amplification. In one embodiment, a plurality of sensors are formed on a single integrated circuit. The sensors may have diverse compositions.

6 Claims, 14 Drawing Sheets

U.S. PATENT DOCUMENTS

| | | |
|---|---|---|
| 4,158,807 A | 6/1979 | Senturia |
| 4,388,532 A | 6/1983 | Garcia |
| 4,439,302 A * | 3/1984 | Wrighton et al. ........ 204/290.11 |
| 4,490,216 A | 12/1984 | McConnell |
| 4,508,613 A * | 4/1985 | Busta et al. ................. 204/418 |
| 4,644,380 A | 2/1987 | Zemel et al. |
| 4,728,882 A | 3/1988 | Stanbro et al. |
| 4,822,566 A | 4/1989 | Newman |
| 4,874,500 A | 10/1989 | Madou et al. |
| 4,935,207 A | 6/1990 | Stanbro et al. |
| 4,968,400 A | 11/1990 | Shimomura |
| 5,071,770 A * | 12/1991 | Kolesar, Jr. ................. 436/151 |
| 5,238,729 A | 8/1993 | Debe |
| 5,289,401 A | 2/1994 | Shima |
| 5,305,231 A | 4/1994 | Coppler et al. |
| 5,345,213 A | 9/1994 | Semancik et al. |
| 5,346,858 A * | 9/1994 | Thomas et al. .............. 438/669 |
| 5,386,715 A | 2/1995 | Evans et al. |
| 5,400,643 A | 3/1995 | De Angelis et al. |
| 5,571,401 A * | 11/1996 | Lewis et al. ................. 205/787 |
| 5,698,089 A | 12/1997 | Lewis |
| 5,736,421 A * | 4/1998 | Shimomura et al. ......... 438/253 |
| 5,918,110 A * | 6/1999 | Abraham-Fuchs et al. .... 438/48 |
| 5,948,464 A * | 9/1999 | Delnick ........................ 427/77 |
| 5,959,191 A | 9/1999 | Lewis et al. |
| 6,077,774 A * | 6/2000 | Hong et al. ................. 438/643 |
| 6,266,110 B1 * | 7/2001 | Mizuno et al. .............. 349/111 |

FOREIGN PATENT DOCUMENTS

| | | |
|---|---|---|
| JP | 53-132981 A | 11/1978 |
| JP | 61-020810 B | 10/1980 |
| JP | 60-067850 | 4/1985 |
| JP | 60-252253 | 12/1985 |
| JP | 61-20811 | 5/1986 |
| JP | 01-053745 | 11/1989 |
| JP | 03-163343 | 7/1991 |
| JP | 06-242038 | 9/1994 |
| JP | 07-501891 | 2/1995 |
| JP | 07-198641 | 8/1995 |
| JP | 07-294405 | 11/1995 |
| JP | 9-236560 | 9/1997 |
| WO | WO 93/22678 | 11/1993 |
| WO | WO 96/07901 | 3/1996 |
| WO | WO 96/30750 | 3/1996 |
| WO | WO 98/07024 | 2/1998 |

OTHER PUBLICATIONS

J.V. Hatfield, et al., "Towards an Integrated Electronic Nose Using Conducting Polymer Sensors," Mar. 1, 1994, pp. 221-228.

Krishna Persaud et al., "Design Strategies for Gas and Odour Sensors Which Mimic the Olfactory System," NATO ASI Series, Series F: Computer and System Sciences, No. 102, pp. 579-602 (1993).

M.E. Hassan Amrani et al., "Multi-frequency Measurements of Organic Conducting Polymers for Sensing of Gases and Vapours", Jul. 1996, pp. 137-141.

Nathan S. Lewis, et al., "Array-based Vapor Sensing Using Chemically Sensitive, Carbon Black-Polymer Resistors", Jul. 1997, pp. 660-670.

* cited by examiner

TECHNIQUES AND SYSTEMS FOR ANALYTE DETECTION

This application is a divisional application of U.S. patent application Ser. No. 10/280,795, filed Oct. 24, 2002, which is a divisional application of U.S. patent application Ser. No. 09/276,988, filed Mar. 26, 1999, which claims the benefit of U.S. provisional application 60/092,707, filed Jul. 14, 1998, and is a continuation of U.S. patent application Ser. No. 09/130,775 and PCT international application PCT/US98/16527, both filed Aug. 7, 1998, and both claim the benefit of U.S. provisional patent application Nos. 60/081,182, filed Apr. 9, 1998 and 60/055,071, filed Aug. 8, 1997, all of which are incorporated herein by reference in their entirety for all purposes.

The research carried out in this application was supported in part by grants from the United States Army (#DAAG55-97-1-0187), DARPA (#DAAK60-97-K-9503), and the National Science Foundation (CHE 9202583). The U.S. government may have rights in any patent issuing from this application.

BACKGROUND OF THE INVENTION

The field of the invention relates to sensor arrays and techniques for the detection of analytes, and in a specific embodiment, electronic techniques and devices for olfaction.

Human beings have at least five senses-sight, smell, taste, hearing, and touch. Since the earliest times, humankind has sought techniques and devices for enhancing and extending these senses. Many of the devices and instruments that have been developed to extend human perception are considered among of the most revolutionary inventions in history. These inventions have had a profound impact on human civilization and have led to many additional breakthroughs and discoveries. Just a few of the many instruments developed to extend the reach of human perception include the telescope, microscope, stethoscope, X-rays, phonograph/radio/audio amplifier, scanning electron microscope, night vision goggles, and many, many others.

As would be expected, there has been considerable interest in developing a device or instrument for general detection analytes in a fluid, vacuum, air, or other medium. A specific instance of an analyte detector is a device for sensing smell or odors (i.e., analytes in air). It is well recognized that some animals like dogs have a keener sense of smell than human beings. Because of their "noses," dogs have a keener sense of smell than human beings. Because of their "noses," dogs have been utilized for many tasks including, for example, the detection of bombs, mines, drugs, poison gases, and illegal contraband; dogs also aid in the search and rescue of humans. Devices for sensing smell would be useful for the traditional applications where animals are used, as well as for a multitude of uses where animals are impractical or inappropriate.

Moreover, a device for the general detection of analytes has potentially many more applications than a specific device for detecting smells. For example, the uses for a device for analyte detection include the detection of chemical leaks, quality control in food processing, medical diagnosis and testing, fabrication and manufacture of commercial and industrial goods, pharmaceutical production, testing or evaluating any odorant or analyte in any medium (e.g., fuel, oil, wine, solvents), and many other applications. An instrument for analyte detection would be highly desirable in industries and applications such as the chemical and petrochemical sectors, food, fragrance, medical, automotive, military, environmental, health and safety, and indoor air quality. Therefore, it is desirable to develop techniques and devices for the detection of analytes.

An approach for sensing smells is to use surface acoustic wave (SAW) resonators. However, the signal transduction mechanism for SAW devices involves relatively complicated electronics, and are thus somewhat costly. Furthermore, SAW devices are generally extremely sensitive to both mass and acoustic impedance changes, and may not be suitable for use in all environments.

Therefore, there is a need for techniques and systems for analyte detection, especially ones that are low cost, easy to manufacture, provide rapid response, and produce accurate differentiation between different analytes and different concentration of the same analyte.

SUMMARY OF THE INVENTION

The present invention provides techniques and a system for detecting and identifying analytes in fluids. The present invention also provides techniques for fabricating and manufacturing sensors to detect analytes in fluids. Analytes may include smells, tastes, vapors, odors, gases, liquids, and chemicals, among others. The fluid may be liquid or gaseous in nature. In the present invention, an analyte is sensed by sensors that output electrical signals in response to the analyte. The electrical signals may be preprocessed by filtering and amplification. This preprocessing may also include adapting the sensor and electronics to the environment in which the analyte exists. The electrical signals may be further processed to classify and identify the analyte.

There are many possible embodiments of an analyte detection system of the present invention. For example, the present invention may be used to implement an electronic olfaction system or "electronic nose." Such a system may reveal the identification and concentration of vapors in a manner similar to the mammalian olfactory system. Another embodiment for the analyte detection system of the present invention may also be used to implement a device for tasting. This device would function similarly to a tongue. There are many other possible embodiments of the present invention, too numerous to name in this application.

In one embodiment, sensors of the present invention are fabricated using semiconductor processing techniques and formed on a single integrated circuit. The integrated circuit or chip may contain a plurality of sensors, each at a sensor site. The sensor sites are formed on a substrate such as silicon, and may be arranged in rows and columns. Structures or other means may be constructed on the substrate to constrain a sensor material at each sensor site. For example, the sensor sites may be a plurality of sensor wells that could hold the sensor material.

The sensor material applied to or formed at one sensor site may have a different composition from the sensor material at a different site. For example, each sensor in the analyte detection system may have a different composition from every other sensor. For example, the sensor material may consist of regions of a nonconductive organic insulating material and a conductive material such as carbon black; the composition of carbon black may vary for each sensor on the chip. By providing a system of diverse sensors, each sensor may have a different response characteristic for a given analyte.

The integrated circuit may also include an electrical connection at each sensor site to route the electrical signals from the sensor material to other circuitry. This circuitry may further process the electrical signals. The circuitry may be on the same chip (on-chip) with the sensors, or may be off the chip (off-chip) carrying the sensors, such as on a different integrated circuit. For example, an analyte detection system of the present invention may include two or more integrated circuits, making up an analyte detection chipset.

In a specific embodiment of the present invention, electronic circuitry resides on the same integrated circuit as the sensor site. In particular, there is circuitry associated with each sensor site, and this circuitry may be formed beneath or interspersed with the sensor sites.

The signals from the sensors may be further processed by classifying the response to the analyte. For example, each analyte may have a particular "fingerprint." The analyte may be identified based on this fingerprint. The signal processing for the identification and classification of the analyte may be performed by on-chip or off-chip circuitry. For example, classification may be performed using a computer or other instrument, among other techniques. Therefore, using the techniques and system of the present invention, an analyte may be distinguished and identified.

An aspect of the present invention is the use of an array of sensors to detect analytes. A further aspect of the present invention is the use of an integrated circuit having an array of sensors to detect analytes. A still further aspect of the present invention is the use of a semiconductor process to fabricate an integrated circuit having an array of sensors for identifying an analyte.

In a specific embodiment, the present invention is an integrated circuit including a plurality of sensor sites formed on a semiconductor substrate, each sensor site for constraining the sensor material. The integrated circuit further includes an electrical terminal formed to measure an electrical property of the sensor material. The electrical property may be a resistance, capacitance, inductance, or other electrical property. The sensor material may be a material consisting of a nonconductive organic insulating material and a conductive material. The sensor site may be a sensor well.

In a further embodiment, the integrated circuit of the present invention includes an array of sensors for detecting chemical analytes, each sensor having a first and second output terminal. There are plurality of adaptive electronic circuits, each circuit associated with one of the sensors and coupled to the first and second output terminals of the associated sensor.

To fabricate a semiconductor structure, a plurality of layers are formed on a silicon substrate. A plurality of wells is created in the plurality of layers. The sensor materials deposited into each well. Further, the composition of the sensor material in each well may be different from the sensor material another well the silicon substrate.

Other objects, features, and advantages of the present invention will become apparent upon consideration of the following detailed description and the accompanying drawings, in which like reference designations represent like features throughout the figures.

DESCRIPTION OF THE SPECIFIC EMBODIMENTS

Figure 1:
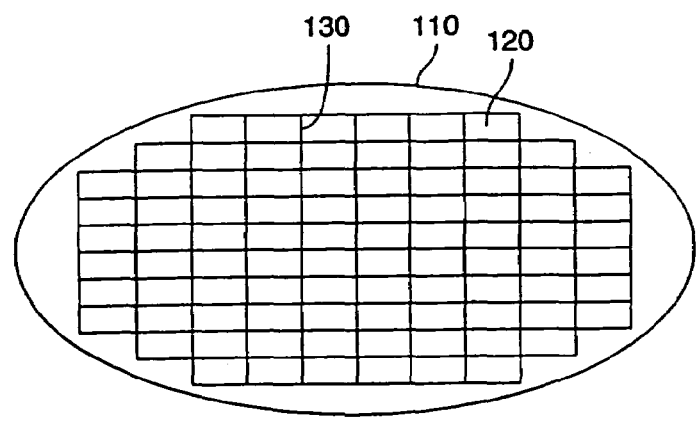
FIG. 1 shows a substrate with a number of analyte detection integrated circuits.

The present invention provides techniques for the detection and identification of analytes. These analytes may be in fluids, which may be liquid or gaseous in nature. The techniques of the present invention may also be used to provide other information about analytes, including for example, the concentration, classification, volume, flow rate, direction of a plume trail, location of source of analyte, gradient, and other characteristics. For example, the techniques of the present invention may allow the determination of the concentration of a first analyte and a second analyte in a mixture.

A system of analyte detection of the present invention has many applications. This system may be embodied within analytical instruments, handheld devices, robots, and many other devices and tools. For example, the system of the present invention may, in a specific implementation, reside on a single integrated circuit or multiple integrated circuits. There are however many other ways to implement a system of the present invention. For example, the system of the present invention may have components which are relatively close in proximity to another, such as being resident on the same substrate, integrated circuit, or printed circuit (PC) board. Alternatively, various components of the analyte detection system may also reside in different locations, and linked by a network or other communications link. This network may include a local-area network, wide-area network, wireless network, cellular phone network, optical network, the internet, electrical wire, and many others, and combinations of these networks.

An example of a specific embodiment of the present invention is an electronic system of analyte detection. In particular, the electronic system of analyte detection may include a plurality of sensors. Further, one sensor in the plurality of sensors may have a different characteristic from another sensor in the plurality. In an even further embodiment, each sensor in the plurality of sensors may have different characteristics from every other sensor. U.S. Pat. No. 5,571,401 discusses sensors and sensor materials which may be used in a system of the present invention, although other sensors and sensor materials may also be used. U.S. Pat. No. 5,571,401 is incorporated herein by reference in its entirety for all purposes.

A technology that has led to the proliferation of modern electronics is the integrated circuit. Integrated circuit technology may be used in an electronic analyte detection system of the present invention. However, the present invention is not necessarily limited to integrated circuit technology, as there are many other technologies for implementing the present invention. For example, the system of the present invention may be practiced using discrete electronic components assembled on s printed circuit board. A system of the present invention may be contained within a handheld electronic device.

Using integrated circuit technology to fabricate an electronic analyte detection device permits relatively low cost and high volume manufacture of such devices. Integrated circuits are the modern marvel of today's electronic and information age. Commonly referred to as "chips," integrated circuits are miniaturized electronic circuits fabricated on silicon substrates. Chips are commonplace in the electronics market, and are the building blocks for a vast number of electronic products used in many industries. Products using integrated circuits include computers, computer peripherals, consumer electronics, telecommunications and networking equipment, and many others.

A system of the present invention may be manufactured using integrated circuit technology. However, the present invention is not necessarily limited to implementations using integrated circuit technology; other technologies may also be used. The present invention is also not limited to electronic olfaction since a system according to the present invention may be used to detect, identify, and classify analytes in a variety of mediums and environments.

FIG. 1 shows an implementation of the present invention using integrated circuit technology. A substrate or wafer 10 has a number of analyte detection chips 120. Similar to the case with integrated circuit fabrication, many analyte detection chips 120 may be formed on a single substrate. There may be hundreds or thousands of such chips on one substrate.

The substrate may be silicon, such as single crystal silicon having a <1 0 0> or <1 1 1> orientation. Other materials may also be used as a substrate including, just to name a few, other semiconductive materials, other materials suitable for the manufacture of integrated circuits, insulators, diamond, silicon (or other semiconductor material) over an insulator (such as sapphire), plastic, fused substrates, and polymers.

Analyte detection chips 120 may be fabricated on the substrate using a semiconductor process typical of the integrated circuit industry. Successive layers of various materials are formed and patterned on the substrate. The layers may include, just to name a few examples, diffusion (n- and p-type), silicon oxide, gate oxide, polysilicon, metal (including multiple layers of metal), contact, and via. These layers may be formed on the substrate by deposition, growth, ion implantation, sputtering, electroplating, and other techniques. Photoresist may be used to pattern the features on the substrate. Features may be etched using dry or wet etching techniques, and combinations of these in the same process.

In one embodiment of the present invention, analyte detection chips are fabricated using a CMOS process technology. Many other technologies may also be used, such as NMOS, BiCMOS, bipolar, and others.

Individual analyte detection chips are formed adjacent to other chips on the substrate. Individual chips are separated from each other by a scribe line 130. In many instances, each analyte detection chip is substantially identical to another. It is however possible to manufacture different types or different designs of analyte detection chips on a wafer. There may also be test die or structures on the wafer to allow testing and evaluation of various process parameters and properties of the analyte detection chips during the fabrication of the wafer. Test structures may also be formed in the scribe lines between the individual dies.

During the manufacture of analyte detection chips, a sensor material is placed on the substrate. For example, this sensor material may be deposited, coated, or otherwise applied on the substrate. In one embodiment, the sensor material is any material which provides an electrical response to an analyte or odorant. For example, an electrical response may be quantified in terms of impedance (R), inductance (L), capacitance (C), or other electrical changes. In an embodiment, the sensor material may be a polymer. The material may be organic, or inorganic in other embodiments. Further, the sensor material may consist of regions of a nonconductive organic material and a conductive material. In other embodiments, the sensor material may be insulating organic films that act as capacitors, or composite films that act as inductors. A more detailed description of some sensor materials and their properties is discussed in U.S. Pat. No. 5,571,401. However, the present invention is not limited to the sensor materials in U.S. Pat. No. 5,571,401 since other materials may also be used.

In a specific embodiment of the present invention, the sensor technology may involve a series of conductive polymeric composite vapor sensors. The presence of an analyte may be detected through a change in, for example, the electrical resistance of a chemically sensitive carbon-based resistor. As discussed above, changes in electrical properties other than resistance may also be used; these include the evaluation of capacitive and inductance changes.

Further, the sensor material may be composed of conductor and insulator composites. This material may be placed on the substrate in a film. The organic nonconducting polymer of the composite absorbs the analyte (which may be a vapor). This induces a change in the electrical properties of the sensor material. The sensor material may also undergo physical changes such as swelling. When the analyte is removed, any changes in the electrical properties reverse. For example, the resistance, capacitance, and inductance may return to their original value. Any physical changes would also reverse. The response of these types of sensors are reversible over multiple analyte exposures as well as reproducible over a large number of trials under a variety of ambient atmospheric conditions. Therefore, a device fabricated using these types of sensor materials would have a relatively long service life.

In the case of using a composite such a nonconducting polymer and carbon black, the sensor material will be temperature sensitive. When using temperature-sensitive sensors, the sensor should be kept at a relatively constant temperature to provide relatively consistent results. For example, a temperature such as about 5° C. above the ambient should provide good results. Further, extremely high temperatures, say, above about 100° C., should be avoided since these temperatures would destroy the polymer sensor material or rapidly decrease its service life. For this reason, it is not expected that nonconducting polymer materials are to be used in the specialized environment of extreme high temperatures, say, from about 300° C. to about 400° C. or even higher. The polymer sensor materials will be usable in the normal temperature ranges from about 0° C. to about 100° C.

Using a conductor and insulator composite for the sensor material permits a very broad, diverse collection of sensor materials: For example, any conducting element including carbon blacks, metallic colloids, or organic conducting polymers, and combinations of these, may be used as the conductive phase of the sensors. Any organic material may be used as the insulating phase of the sensors. Furthermore, an advantage of these types of sensor materials is that they do not have the stability limitations of conducting organic polymeric materials. A conductor and insulator composite also does not suffer the limitations from the types of substituents or restrictions on the ranges of swelling variations that can be obtained from backbone modification of pure organic conducting polymers.

After processing of a substrate or wafer is complete, the wafer is tested to determine the number and location of the "good" die. The percentage of good die on one wafer compared to the total number of die on the wafer is referred to as the "yield." Individual analyte detection dies are separated by sawing along the scribe lines. The analyte detection dies are then packaged, and may be further tested to ensure their proper operation. These dies may be packaged in a variety of packaging material including ceramic, epoxy, plastic, glass, and many others. Packaged analyte detection die may very much resemble packaged integrated circuit chips. For some types of applications, nonporous, nonreactive materials like ceramic may be used.

In one embodiment, the sensor material is deposited or applied at the wafer level, before individual dies are separated. In other embodiments, the sensor material is applied after the dies are separated.

Figure 2A:
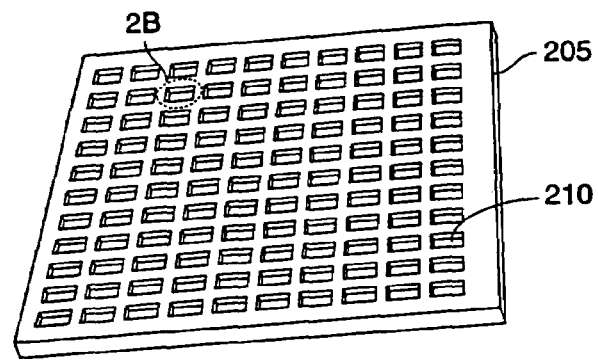
FIG. 2A shows a more detailed diagram of one analyte detection integrated circuit.

FIG. 2A shows a more detailed diagram of an analyte detection chip 205. In a basic embodiment, an analyte detection chip of the present invention includes a plurality of sensor sites 210 of sensor material. In the present invention, the sensor material is constrained by some means at each sensor site. There are many techniques of constraining the sensor material at specific sites on the substrate. For example, the sensor material may be constrained at specific sites by surface tension. The sensor material may also be constrained by an electrical charge, electric field, or magnetic field. Further, the sensor material may be constrained using structures formed by integrated circuit processing techniques or other techniques (e.g., micromachining or microelectromechanical systems (MEMS)). Examples of these structures include sensor wells, ridges, trenches, circular structures, towers, and many structures to constrain the sensor material at the sensor sites. These structures may be fabricated on or in the substrate.

Figure 2B:
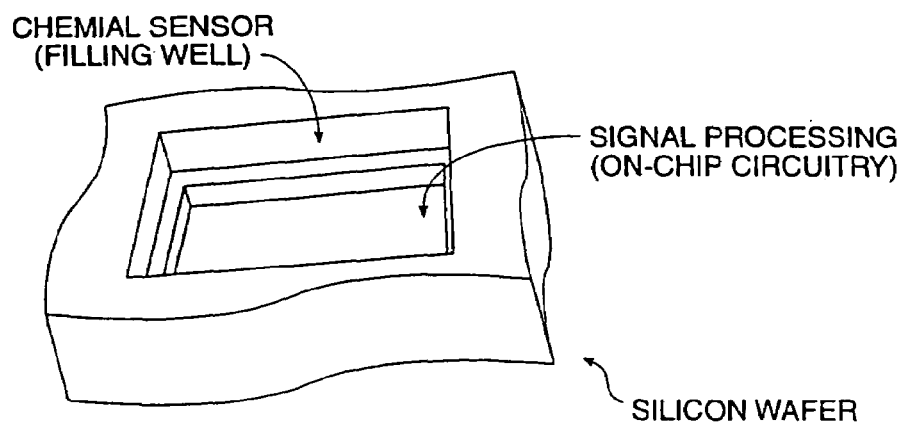
FIG. 2B shows a detailed view of a sensor well.

In the specific embodiment shown in FIGS. 2A and 2B, sensor wells are used to constrain the sensor materials at the sensor sites. FIG. 2B shows a more detailed view of a single sensor well. In the typical case, the sensor material may be deposited in the sensor wells of the analyte detection chips at the wafer level, before the chips are separated from the wafer. The sensor wells, however, may also be filled after the individual chips have been separated from the wafer. As discussed above, other techniques may be used to form the sensor sites and constrain the sensor material, and sensor wells are shown merely as an example. Other structures may be used in a similar fashion to constrain the sensor material.

For the analyte detection chip in FIG. 2A, the sensor sites are arranged in an array having rows and columns of 11 sensor sites by 11 sensor sites, for a total of 121 sensor sites. As discussed above, the sensor sites in FIG. 2A are sensor wells. Sensor material will be applied at these sensor sites which will serve as the analyte detection sensors.

The analyte detection chip depicted in the figure will have 121 sensors. In other embodiments, the analyte detection chip may have fewer than 121 sensors. For example, an analyte detection chip may have a two sensor sites, three sensor sites, four sensor sites, or greater number of sensor sites. An analyte detection chip may have two, three, four, five, six, seven, or more sensors sites for sensors. The chip may have ten to twenty, twenty to thirty, thirty to forty, forty to fifty, and fifty to one hundred sensors. A specific embodiment of the analyte detection chip has thirty-two sensor sites. Even more complex analyte detection chips may have many hundreds or thousands of sensors. For example, a chip may have 10,000 sensors (possibly arranged in an array with 100 sensors per side).

The array of sensors may be arranged in many possible formats, and may have an equal number of sensors per side. The arrangement of the plurality of sensor sites may be selected as appropriate for a particular application.

Although FIG. 2A snows a square array arrangement of sensor sites, the sensor sites may be arranged in any fashion on the chip. For example, the plurality of sensor sites may be arranged in an oblong or rectangular structure, triangular structure, circular or curved structure, and many other arrangements. An array of sensor sites may have 1 site by 10 or more sites, 2 sites by 10 or more sites, 3 sites by 10 or more sites, 10 sites by 20 sites, or 30 by 175 sensors, just to mention some examples. There may also be multiple arrays or multiple groupings of sensor sites on the same substrate. There may be two, three, four, five, or more arrays of sensors on a single substrate.

Figure 2C:
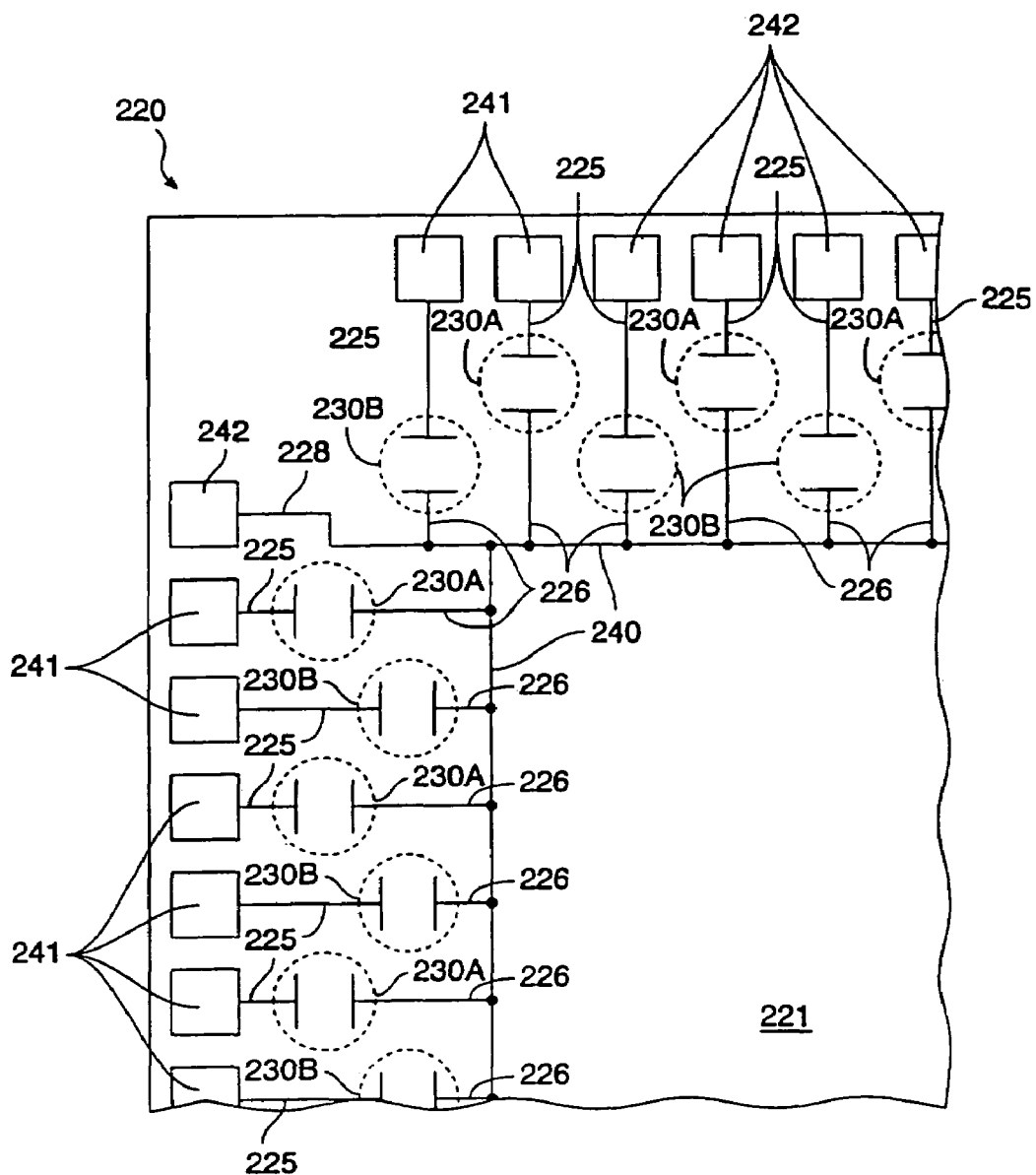
FIG. 2C shows an embodiment of the present invention in which a detection chip is formed with only a single conducting layer.

FIG. 2C illustrates one embodiment of the present invention in which a detection chip 220 is formed with only a single conducting layer formed over a substrate 221. The single conducting layer, typically of metal, such as aluminum and its compounds, advantageously allows for a simple semiconductor process. The simpler processing provides for quicker manufacturing times and a reduced number of failure mechanisms. On the other hand, the simpler processing creates constraints in the layout of the chip 220 and necessarily creates a chip with some functional simplification.

The chip 220 provides for a number of sensors 230A and 230B around the periphery of the substrate 221. Only one corner of the substrate 221 is shown. The sensors 230A and 230B are arranged in two rows and are representationally illustrated by a dotted circle and two spaced-apart and parallel line segments. The dotted circle represents sensor material and the two line segments represent the electric terminals by which a reaction of an electrical parameter of the sensor material to an analyte or odorant is received. Each terminal is connected to one of two conductive leads 225 and 226, one lead 226 connected to a common line 240, i.e., a reference line, and the other lead 225 connected to a bonding pad 241. The common line 240 is arranged as an annular ring around the substrate 221 on the inside of the peripheral rows of the sensors 221A and 221B. By a lead connection 228 to a bonding pad 242, the voltage level of the common line 240 is fixed. As seen in FIG. 2C, the two rows of sensors 231A 2nd 231B are arranged in staggered fashion which allows the optimum packing of the sensors. The dotted circle of each sensor 230A and 230B also indicates the possible area covered by the sensor material described previously.

This arrangement permits electrical signals from each sensor 230 through the sensor's bonding pad 241 and the common bonding pad 242. The signals may be derived directly from the electrical characteristics of the sensor material or may be signals which have been preprocessed by the electrical circuits associated with each sensor 230, as described below. In either case, this arrangement can be implemented by "a single-metal layer" process, a term well understood in the semiconductor industry. Processing and layout is advantageously straightforward. With semiconductor technology readily available today, a chip with 32 sensors is easily manufactured. The surface is treated with gold to assure good contacts.

In other embodiments, a system of analyte detection may use sensors that reside on separate substrates. For example, the analyte detection system of the present invention may gather analyte information from sensors in different physical locations such as sensors located at various positions of a production line or different rooms within a building.

Figure 3:
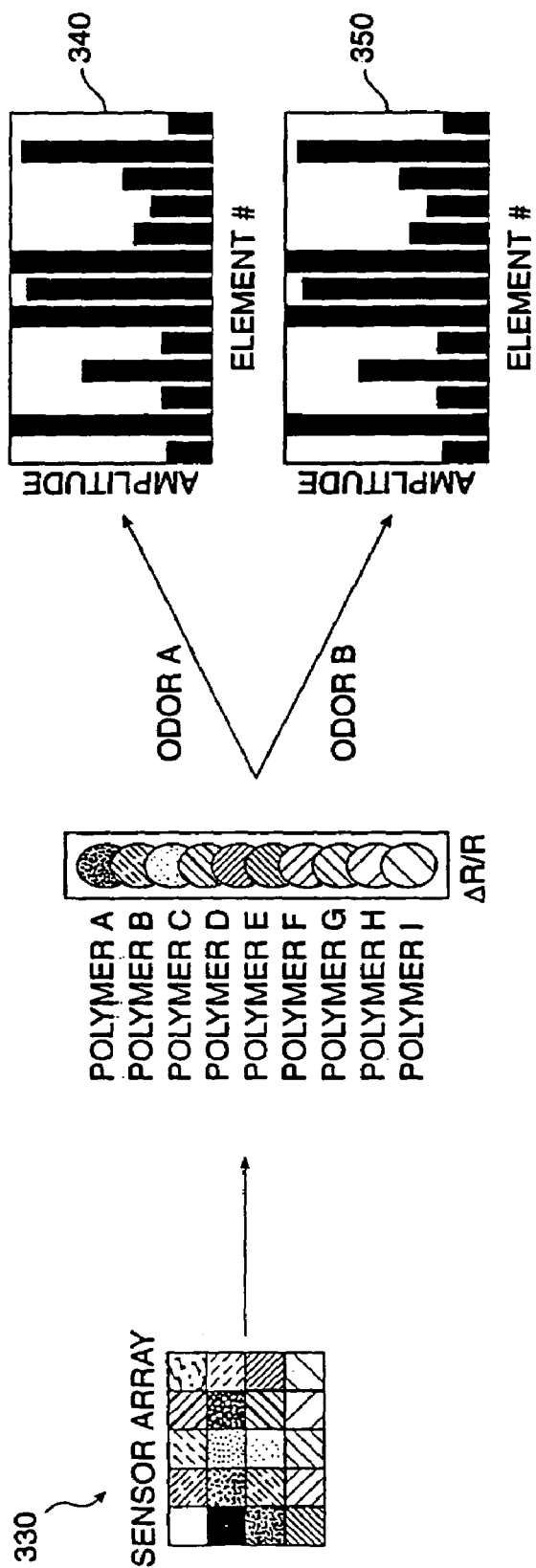
FIG. 3 shows how a sensor array including a collection of different sensors may be used to identify an analyte.

FIG. 3 shows how a plurality of sensors 330 of the present invention may be used to identify an analyte. In an embodiment, the sensors would be formed on a substrate at sensor sites, and these sites may be arranged in an array form as discussed above. Each of the sensors may be incrementally different, and each is not specifically responsive to any particular analyte. For example, each sensor may have essentially a different polymer composite resistance change (listed as polymer A through polymer I) from every other sensor. When two analytes, such as odor A and odor B, are evaluated using the collection of sensors, the result will be two different response patterns 340 and 350. Each analyte has a characteristic "fingerprint." Pattern recognition processing may then be used to identify the analytes on the basis of these patterns.

In an embodiment of the present invention such as shown in FIG. 3, every sensor has a different composition of sensor material from every other sensor. This may be referred to as "sensor diversity." In other embodiments of the present invention, however, there may be multiple sensors in a sensor array that are the same. In other words, some groups of sensors in this embodiment will be manufactured with exactly the same composition, while other groups of sensors will have a different composition. Having two or more of the same sensors in a sensor array may serve a redundancy purpose, which may be useful to increase the production yield. Redundancy in sensors may be useful for increasing the service life or reliability of an analyte detection chip, especially when used in harsh environments (e.g., industrial) or mission critical situations (e. g., military, bomb detection, or use by a common carrier). The techniques of the present invention for analyte detection also apply to cases where similar sensors exist in an array of sensors.

An aspect of the present invention is the use of a plurality of sensors having different response characteristics to distinguish and classify analytes. These sensors may be formed on the same substrate. The plurality of sensors will give a multidimensional response for use in characterizing and classifying the analyte.

A particular sensor material may be broadly responsive in the presence of many analytes. A response or signal from one sensor allows detection of a change in the composition of an analyte, but does not necessarily allow identification of that analyte. An array of sensor elements provides a reversible, diagnostic pattern of changes in an electrical parameter (such as resistance, capacitance, or inductance) upon exposure to different analytes. When a number of sensors with diverse chemical compositions is used, an analyte will have a particular fingerprint or signature.

Correlations between the elements of a sensor array may require many more than two sensors to successfully distinguish molecules in a complex environment. A greater number of sensors generally allows the identification of a greater number of analytes. Moreover, a greater number also decreases the chance that two analytes will have a similar or the same fingerprint. The sensitivity of an analyte detection system depends in part on the number of sensors, and diversity of the sensors. The analyte detection system of the present invention may be related to a biological analog, the nose. It is believed the human olfaction system has about $10^6$ total sensors of about $10^3$ different types of receptors. As is well known, dogs have a keener sense of smell than humans. A canine's nose has about $10^8$ sensors, which is two orders of magnitude greater then the human nose.

Greater numbers of sensors may be useful in a number of ways. It may be beneficial to measure the same property in many different ways due to noise limitations in a practical system. For example, if sufficient precision could be obtained, it might be possible to identify uniquely any molecule merely from a 38-bit measurement using two sensors. But in practice, it may not practical to make such precise measurements. Hence, when using lower precision measurements, useful information on the nature of the analyte may be obtained by making measurements using many independent determinations from many different sensor elements (such as in a sensor array).

Furthermore, a limited number of sensors may be sufficient to distinguish between a series of pure substances that are maintained at a fixed, known concentration. However, if the background is unknown, if mixtures are present, or if the background gases are changing in concentration, many more sensors may be needed simply to avoid ambiguity in interpretation of the output signal pattern. Even more sensors may be needed if optimal discrimination is to be accomplished between a given target signature and a wide possible range of background clutter. Having large numbers of sensors also allows redundancy and provides the ability to reject or veto the output of poorly performing sensors.

Having greater numbers of sensors may also improve a signal-to-noise response or reduce the time required to identify an analyte. It is possible to achieve signal-to-noise ratio gains from averaging over a large number of sensors during a given observation time. Therefore, with 10,000 sensors, for example, a $n^{1/2}$ signal-to-noise ratio gain would yield an effective sensitivity increase of almost two orders of magnitude over the capabilities of 1 to 10 sensors.

Because of all of these issues, the number of sensors to successfully sense and identify an analyte in a practical device may rapidly multiply from a minimum value. A main goal of array-based sensing is to insure that no two analytes will have the same fingerprint response from the array, and also that a given target pattern is not confused as a mixture of other, unanticipated or unknown, background components. Therefore, it is generally desirable to integrate large numbers of sensors into an array structure. The present invention permits the manufacture of a large number of sensor elements in a low-cost, parallel process. And, the processing allows sensor elements to be chemically diverse.

An array of six to eight sensors is sufficient to adequately distinguish between analytes. This is the case when the electronics used with the sensors provides adequate accuracy, such as a very precise analog-to-digital converter. As the number of sensors increases, fewer bits of accuracy will be required to distinguish between analytes as discussed above. For example, with sixteen to twenty sensors, less precise electronics are needed. With the integrated circuit technology available today, one practical implementation of an analyte detection chip has thirty-two sensors. Signals from thirty-two sensors may be decoded and processed by electronics using an analog-to-digital converter with about twenty bits of accuracy. This is not unduly complicated or prohibitively costly to implement. As integrated circuit technology improves, it is expected that it will become practical to fabricate more than thirty-two sensors on a single integrated circuit, and to process the signals from these sensors.

The chemical sensor material is applied at a sensor site. The chemical sensor material has electrical properties that can be measured in terms of electrical parameters. These parameters may be resistance, capacitance, or inductance. In the presence of an analyte or odor, the chemical sensor material will have a measurable response characteristic. A change or pattern of changes in the electrical properties of the sensors in sensor array may be measured to identify a particular analyte.

By evaluating a change in, for example, the resistance of the sensor material, an analyte detection system of the present invention may identify an analyte. A particular sensor may have a baseline resistance of 50K ohms (R1). However, when the sensor is placed in the presence of an analyte such as water vapor or hexane, the resistance of the sensor may change to 51K ohms (R2). This change in the resistance (i. e., (R1−R2)÷R1) relative to the baseline resistance value may be used to identify the analyte. The baseline resistance value is used as a reference point. The value of baseline resistance may vary depending on the operating conditions of the sensors such as the pressure, temperature, and humidity. The baseline resistance may also vary because the background ambient may change. For example, there may be background analytes which are not of interest and should not be considered during any measurements.

Changes in electrical properties other than resistance of the sensor material may also be measured and similarly analyzed. Resistance has been discussed merely as an example. A change in the capacitance or inductance of the sensor material may be measured to identify an analyte. In the presence of an analyte, the capacitance change of the sensor material (which may be due to a physical swelling of the material) may be measured.

A composition of the sensor material may determine its response characteristic. A sensor in a first position in the array may have a slightly different composition from another sensor in a second position in the array. The two sensors will give different response characteristics, and this difference may be used to help distinguish different analytes or odorants. For example, if a mixture of a nonconductive and conductive polymer is used as the sensor material for an array of sensors, the composition of the sensors may be different. In an embodiment where carbon black is used, the carbon black composition of each sensor may be slightly different from other sensors in the array.

In addition to the sensor sites for constraining the sensor material, the analyte detection chip of the present invention may include electrical or other connections to the sensor material at the sensor sites. For example, in the case when resistances of the sensors are to be evaluated, conductive layers such as metal may be used to connect with the sensor material in a similar fashion as metal interconnect is used in a semiconductor chip. In the case when capacitances are to be evaluated, a conductive material may be placed in proximity to the sensor material to allow capacitive coupling and sensing. The electrical signals from the sensor may then be routed to bonding pads of the analyte detection chip. Via the bonding pads, the electrical signals from the sensors may be connected to off-chip circuitry for further processing and analysis.

Figure 4:
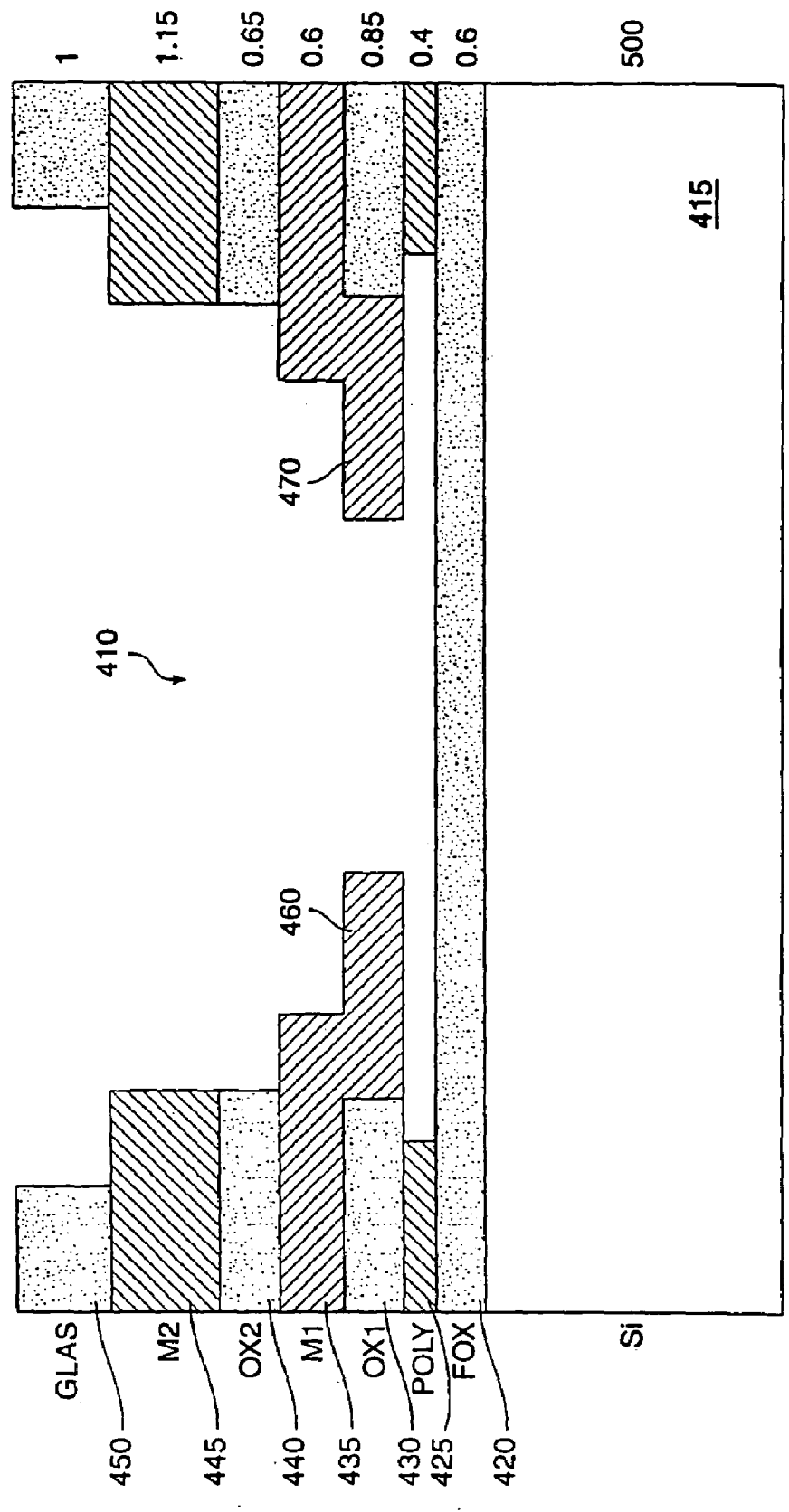
FIG. 4 shows a cross section of a sensor well.

As discussed above, in a specific embodiment of the present invention, sensor wells constrain the sensor material. FIG. 4 shows a cross section of an implementation of a sensor well. This sensor well may be fabricated on a silicon substrate using a CMOS process. The sensor material will fill and be constrained by a sensor well 410. On a silicon substrate 415, the following layers may be patterned and used to form sensor well 410: a field oxide (fox) layer 420, a polysilicon (poly) layer 425, a first oxide (ox1) layer 430, a metal-1 (M1) layer 435, a second oxide (ox2) layer 440, a metal-2 (M2) layer 445, and a passivation or glass (GLAS) layer 450.

An example of a process flow for fabricating a sensor well is as follows. An oxide layer is formed over a silicon substrate. A metal or conductive layer is formed on the oxide layer. The metal layer is patterned and etched. The resulting metal is to be used as contacts for the sensor material. An oxide layer is formed on the structure. A sensor well is patterned and etched. The sensor material is deposited in the sensor well and is in electrical contact with the patterned metal layer.

In one embodiment, the sensor material is applied to the sensor well after the sensor well is formed as a step during the fabrication of the chip (before the formation of the passivation layer). For example, the sensor material may be applied at the semiconductor fabrication facility. However, in other embodiments of the present invention, the sensor material may be applied in a postprocessing step, after the fabrication of the chip. For example, the sensor material is applied after the completed wafers are received from the semiconductor fabrication facility.

In one embodiment, the silicon substrate 415 is about 500 microns thick. The field oxide layer 420 is about 0.6 microns thick. The polysilicon layer 425 is about 0.4 microns thick. The first oxide layer 430 is about 0.85 microns thick. The metal-1 layer 435 is about 0.6 microns thick. The second oxide layer 440 is about 0.65 microns thick. The metal-2 layer 445 is about 1.15 microns thick. The passivation layer 350 is about 1 micron thick.

Although the structure in FIG. 4 is fabricated using a two-layer metal process, a sensor well may be fabricated using a single-layer metal process and also processes having more than two layers of metal. For example, a sensor well of the present invention may be fabricated in a process having three, four, five, or more layers of metal.

Electrical connections 460 and 470 are formed in the metal-1 layer to make electrical contact with the sensor material. These electrical connections are used to route the sensor signals to other circuitry for further processing of sensor data. This circuitry may be on-chip or off-chip. The metal conductor used to form connections 460 and 470 is typically a conductive material such as gold, platinum, aluminum, or copper. The material for the electrical connections 460 and 470 should be selected so they are not reactive to the sensor material. In the case when the sensor material is applied during a postprocessing step, connections 460 and 470 will be exposed, and a conductive material such as aluminum may easily oxidize. This may result in poor electrical connections to the sensor material.

Good electrical contacts are more important for some embodiments of the present invention than others. For example, a good physical contact may be important when measuring the resistance of the sensor material. This is especially true in cases when the sensor material has a relatively low resistance when compared to the contact resistance. In other cases, such as when measuring capacitance, connections may be made by using a capacitive connection, where there is no physical connection between the sensor material and the conductive material or metal. Consequently, in such an embodiment, there would be fewer concerns associated with oxidation of the metal connection.

The metal-1 layer may be, for example, postprocessed or at least finished in a nonstandard integrated circuit fashion. The surface of standard integrated circuit metalized is normally covered by a thin, air forming, "native" oxide layer. Aluminum, the most popular standard metal, forms aluminum oxide continuously over its surface very quickly when exposed to air. Polymer/carbon black composite resistors can not be taken to high temperatures nor can they be energetically formed in other ways to break through the "native" oxide. As such, a means for good contact to the metal layer must be made. This could be accomplished by chemically or physically etching the exposed electrodes and keeping the metal-1 in an oxygen-free environment while applying the polymer composite sensor material. More practically, an additional layer, or multiple layer sandwich, whose exposed layer is a noble (nonoxidizing) metal may be deposited through any number of techniques on the surface of metal-1. This technique could be physical vapor deposition or chemical vapor deposition or plating amongst others. The technique of sputtering a gold contact layer over a chromium glue layer, followed by photo lithographically defining the metal sandwich is especially attractive.

The circuitry receiving the sensor signals from connections 360 and 370 may be off-chip or on-chip. The other circuitry may include preprocessing, amplification, and classification of the sensor data. Depending on the packaging technology used, bonding pads may be formed along the periphery or edges of the chip, or may be distributed inside the chip (e.g., when using flip-chip packaging technology).

The sensor well structure of FIG. 4 may be used to constrain and allow measurement of the sensor material The sensor material fills or partially fills sensor well 410, and resistance is measured using electrical connections 460 and 470.

Figure 5:
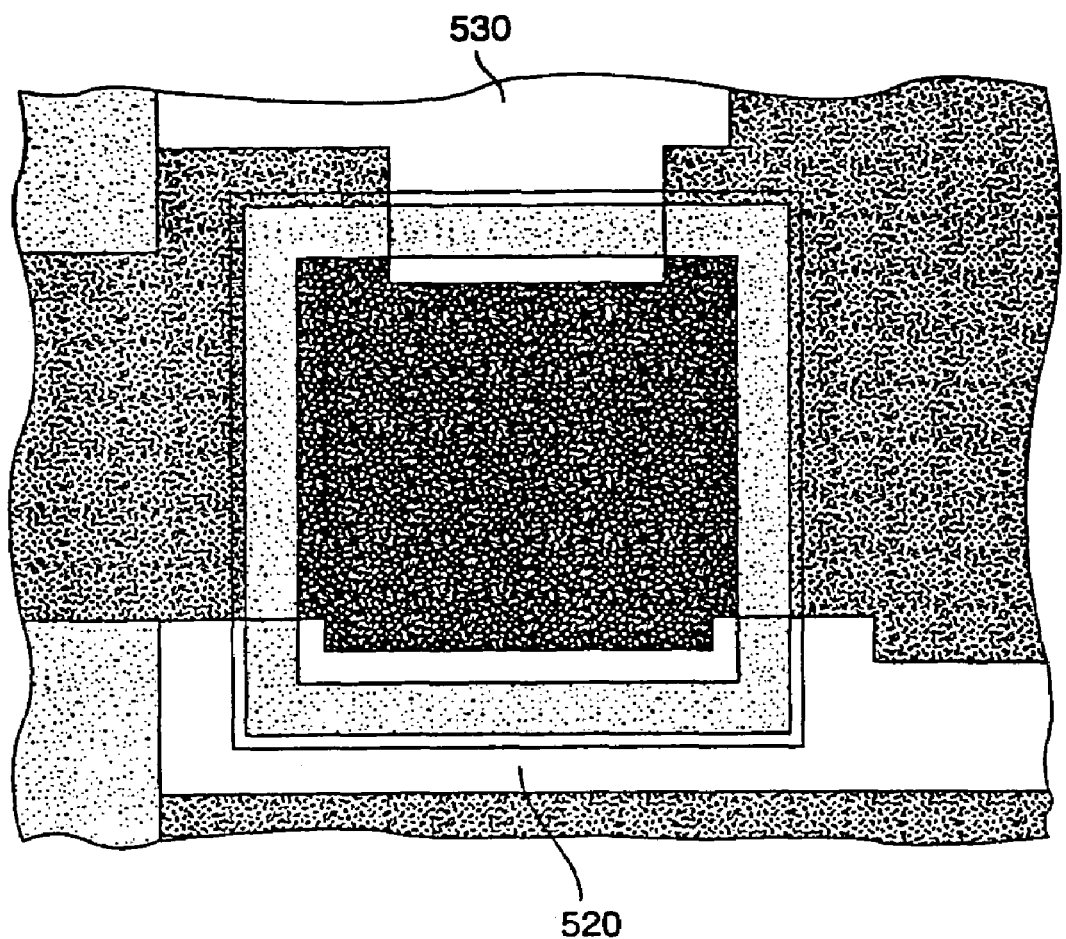
FIG. 5 shows a top view of a layout of a sensor well.

FIG. 5 shows a top view of a 200-micron by 200-micron sensor well structure. Metal is used to make electrical connections 520 and 530 at opposite ends of the sensor well.

Figure 6:
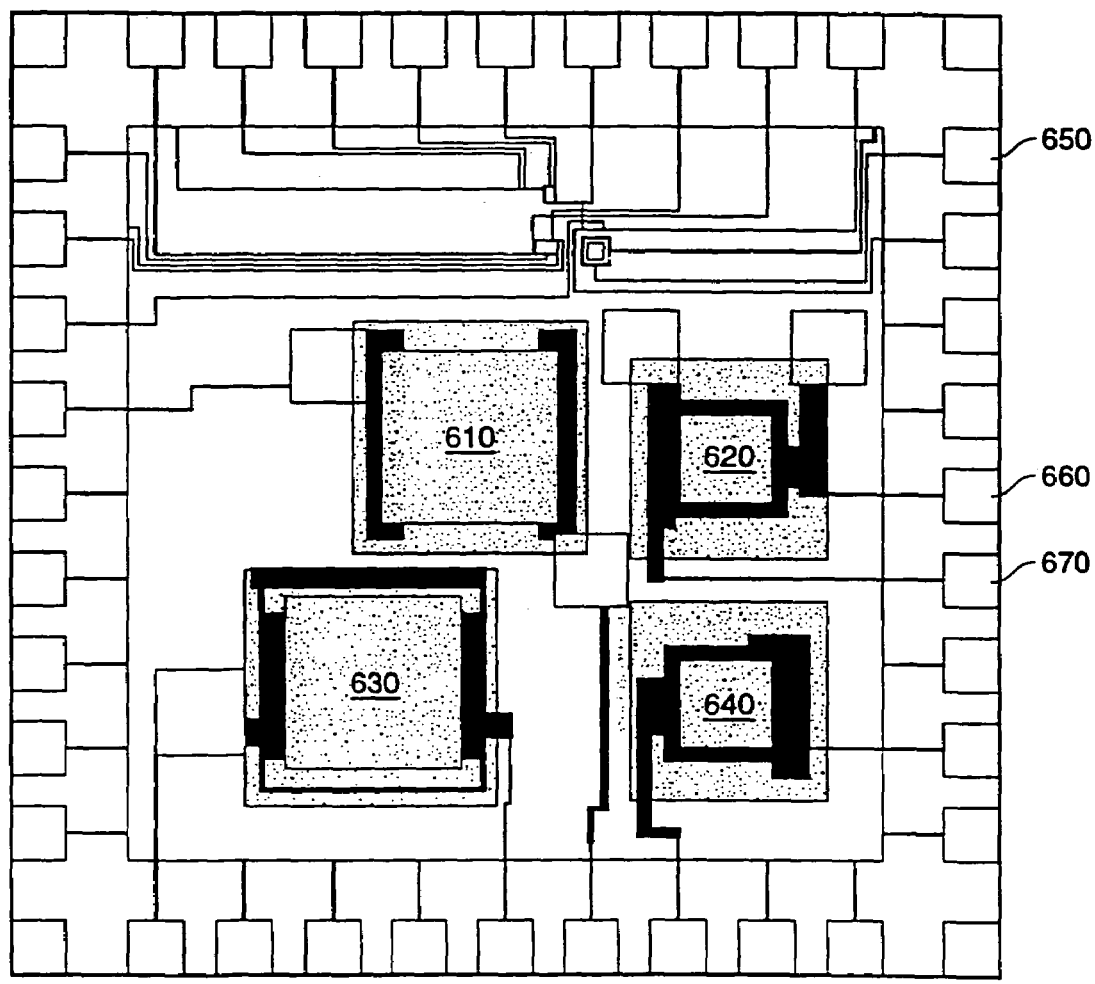
FIG. 6 shows a layout of an integrated circuit with a number of sensor wells.

FIG. 6 shows a layout of a test structure with four sensor wells 610, 620, 630, and 640. These sensor wells are of various sizes. Specifically, sensor wells 620 and 640 are squares of 200 microns per side while sensor wells 610 and 630 are squares of 400 microns per side. Bonding pads 650 surround the four sensor wells and are electrically connected to the censor wells. Two bonding pads or electrical connections may be used to connect to a particular sensor well. For example, pads 660 and 670 connect to the two terminals for sensor well 620. One bonding pad or electrical connection may be shared between two different sensor wells.

Figure 7:
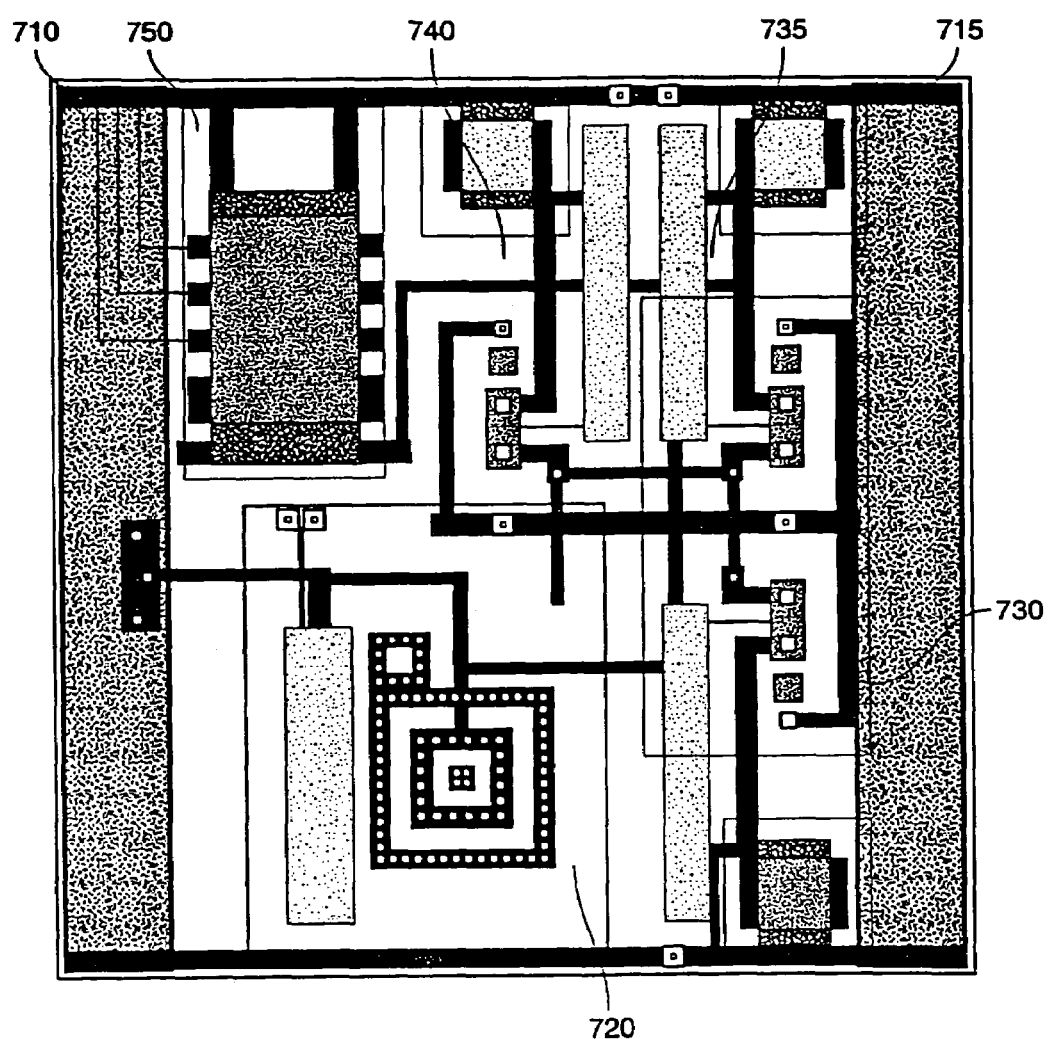
FIG. 7 shows a top view of a layout for a sensor site, where electronic circuitry is formed beneath the sensor site.
Figure 8A:
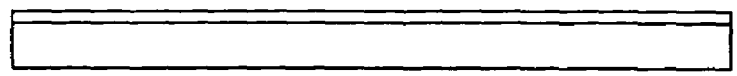
FIGS. 8A through 8F show the different stages in a process of fabricating sensor site and depositing the sensor material.
Figure 8B:
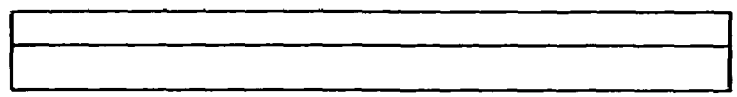
Figure 8C:
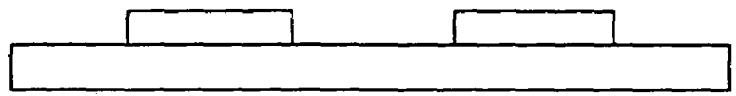
Figure 8D:
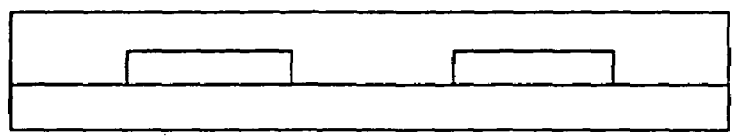
Figure 8E:
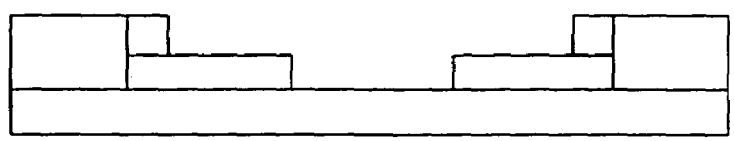
Figure 8F:
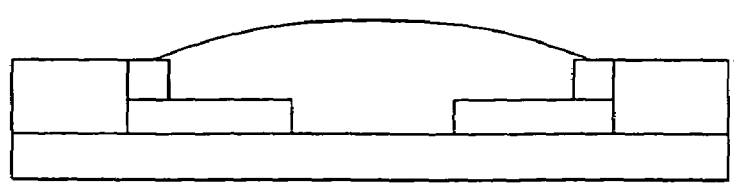

FIG. 7 shows a further embodiment of the present invention where electronic circuitry is formed below or beneath the sensor site. The figure shows a top view of a layout of the electronic devices at a sensor site. Electrical contacts 710 and 715 make electrical contact between the sensor material and electronic circuitry. In this case, the electronic devices implement a preprocessing circuit.

More specifically, the preprocessing circuit may include an autozeroing adaption circuit with signal amplification and X-Y decoding. The individual circuit blocks include a sensor read-out amplifier with baseline adaption circuit 720; signal amplification circuits 730, 735, and 740; and a row/column select and final output amplification circuit 750. In other embodiments of the present invention, however, electronic circuitry for any purpose may be implemented at or beneath the sensor site. Outputs from the electronic circuitry may be routed to other on-chip circuitry, or off-chip circuitry via the bonding pads.

In FIG. 7, the sensor site is a 200-micron by 200-micron sensor well. However, as discussed above, in other embodiments of the present invention, the sensor material may be constrained at the sensor site using a structure or technique other than a sensor well. Furthermore, in other embodiments of the present invention, electronic circuitry is not necessarily formed beneath the sensor site, and may be placed anywhere on the same integrated circuit chip. For example, electronic circuitry may be formed adjacent to the sensors, or in another location on the chip. However, an advantage of forming electronic circuitry beneath the sensors is that the resulting layout is relatively compact.

A cross-sectional structure for the embodiment of FIG. 7 may be similar to what is shown in FIG. 4 where the electrical devices are formed using metal-1 and polysilicon layers. To be able to form electrical devices beneath the sensor well, the second oxide layer will not be etched through. The second oxide layer will instead form a "bottom" for the sensor well. The metal-1 layer is used to electrically connect to the sensor material at the sensor site.

FIGS. 8A through 8F show the different stages in the microfabricating a sensor well structure. The technique shown in FIG. 8A through 8F may be an alternative to a CMOS semiconductor process. For example, the process may be a MEMS or microelectrical fabrication process or other specialized VLSI process. The process may include micromachining to form the structures to constrain the sensor material.

The process can be self-standing (with no underlying electronic circuits) or done in combination with other layers underneath the sequence of layers shown added in FIGS. 8A through 8F. A starting wafer or substrate is shown in 8A. This layer is either an insulating substrate or a starting wafer to which has been added an insulating film. This can be either through oxidation (for a silicon substrate) or deposition. A conductive film may be deposited onto the insulating surface by either physical or chemical vapor deposition methods shown in FIG. 8B. The metal or conductive film is patterned in FIG. 8C leaving a pair of electrodes. An additional insulating film is deposited in FIG. 8D and patterned to expose the electrodes of a nonoxidized metal structure in FIG. 8E. Into the well defined by the top insulator film and between the two electrodes in the bottom of the well, is deposited the sensor material shown in FIG. 8F.

Sensor materials of diverse compositions are applied at the sensor sites of the chip. There are many techniques of applying the sensor material at the sensor sites. For example, the sensor material may be deposited at the sensor sites by using solution spin coating or deposition of monomers and then polymerizing them. In an embodiment where the sensor material are polymer-based chemiresistors, the polymer-based chemiresistors may be formed by spin- or dip-coating substrates with solutions or suspensions of the chemiresistor components. Furthermore, for the case of spin-coated layers or for the case of dip-coated layers, the need for diversity dictates there be a patterning of the first sensor material followed by the application and patterning of many subsequent layers. While not unfeasible, the number of times that this process need be repeated is dictated by the degree of diversity that is desired in the sensors.

Another technique to produce sensor sites containing sensor materials with diverse compositions is to deposit the sensor material serially in time. This will involve making a first deposition at a site which contains a distinct chemical composition from the second, from the third, and so forth.

A still further technique for applying the sensor material is to use microjet or ink jet technology. Ink jet technology is increasingly being used in the fabrication of devices. With such technology, it is possible to fabricate polymeric structures on the order of 100 microns and arrays of these structures with packing densities of greater than 15,000 per square centimeter. Microjets may be useful tools in fabricating large arrays of miniaturized sensors for analyte detection.

For example, to fabricate a diverse set of sensors on a substrate, a continuous jet system may be employed because the composition of the "ink" (e. g., the sensor material which may be a chemical polymer) can be continuously changed. This allows for the fabrication of sensor material films with variable composition from a limited feedstock of monomers or polymers as desired. The monomers delivered into the sensor sites would be polymerized in situ in a subsequent step through exposure to gamma irradiation, to a suitable free radical catalyst or by exposure to light. In this fashion, it will be possible to prepare libraries of thousands of different polymers from uncorrelated monomeric precursors, and to rapidly evaluate their efficacy in distinguishing the analytes of concern.

When using microjet technology, it is important to prevent the ink jet nozzles from clogging. It is desirable for the particle size of the ink be smaller than the nozzle size. In a specific embodiment, microjet technology may be used to apply polymers with carbon black. In fact, classic black inks (such as India ink) are carbon black suspensions. The nozzle size of commercial ink jets is generally greater than ten microns. Since a stable carbon black suspension with particle sizes of less than one micron may be formed, it is possible to fabricate carbon black suspensions compatible with microjet technology.

In addition to standard electrostatically controlled continuous flow or drop-on-demand systems, other options are available. Mechanically controlled ink jets with larger nozzles, essentially small spray guns, may also be used. Another microjet technology is the compound ink jet. With such a device, a jet of the so-called primary fluid emerges from a 10- to 20-micron orifice submerged in a so-called secondary fluid. The resulting jet consists of both fluids, and can be manipulated as in a standard electrostatically controlled continuous ink jet. Compound jets can utilize carbon black based inks, such as India ink, as a secondary fluid since the reservoir for this fluid can be of arbitrary size.

Although the above techniques for manufacturing are highly desirable for some applications, in other applications such as those that include a large numbers of sensor elements in the array, another embodiment of the present invention may be more desirable. FIG. 7G shows a cross section of a portion of an integrated circuit 700 according to this further embodiment. An advantage of this method is that it is highly flexible, and might be used with any number of different base integrated circuit processes. For example, this method is especially useful for those applications which require addressing the array a bit at a time, because many such addressable array architectures have been developed in silicon technology, and this technique allows one to make use of these previously developed infrastructures.

Figure 9:
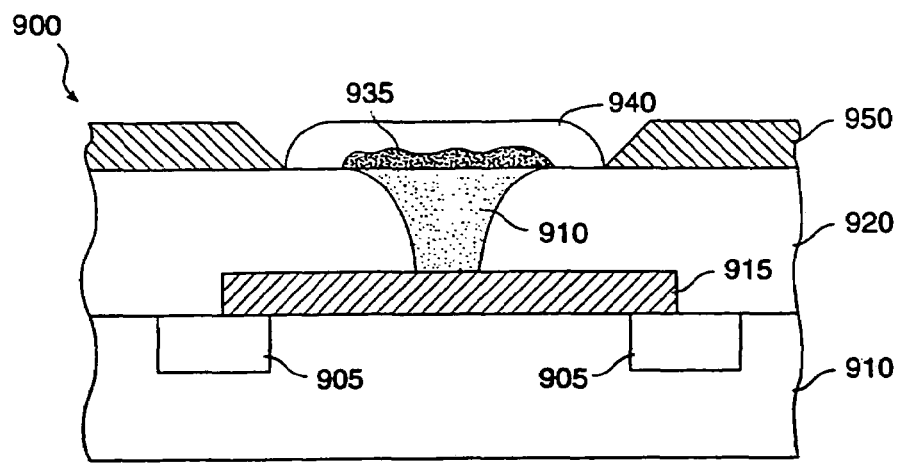
FIG. 9 shows a cross section of an embodiment of a sensor site formed by planarizing an insulator layer.

Referring to FIG. 9, a plurality of semiconductor devices 905 are formed within a substrate 910 by any conventional VLSI fabrication processes, as is well-known in the art. Conductors 915 are formed in a conductive layer to interconnect semiconductor devices 905 and to provide routing to the various sensors. Semiconductor devices 905 and conductors 915 are interconnected to form the various electronics on integrated circuit 900. For example, they may form the electronics for addressing and activating an array of sensor elements. Conductors 915 may be, for example, polysilicon, metal (e. g., aluminum or copper), or other conductive layers. In an embodiment of the invention that measures the change of resistance of a sensor, two layers of metal (not shown) are used for a bias to be generated and current measured at a given X-Y location in the array. Since the information that provides a signal is the change in the resistance of a node, the access lines can be relatively high impedance without causing any serious loss of signal or inducing much additional Johnson noise. Hence, the polysilicon layer, available in every CMOS technology, is usable. In a typical scenario, with a hundred squares of resistance at 10 ohms per square, a polysilicon line might be on the order 1000 ohms of fixed resistance in series with the signal resistor.

An insulator layer 920 of $SiO_2$, $SiO_xN_4$, or other insulating material is formed above semiconductor device 910. Insulator layer 920 electrically isolates semiconductor devices 910 and conductors 915. Contacts 730 are formed within insulator layer 920 to allow electrical connections to conductors 915, and may be formed of a variety of conductive materials such as tungsten or other refractory metals. Although only one contact 930 is shown in FIG. 9 for simplicity, it will be recognized that each sensor may have more than one contact 930 connected to it, for example, to use the contact as a resistive element between two conductors.

After contacts 930 and insulator layer 920 are formed, integrated circuit 900 is planarized to provide a substantially flat surface. The planarization may be accomplished, for example, using chemical-mechanical processing (CMP), a technique well known in the art of integrated circuit processing. By so doing, contacts 930 are exposed. Contacts 930 having exposed metal may be covered with an optional noble metal coating 935 through physical vapor deposition, chemical vapor deposition, or plating techniques to provide an optimal electrical contact.

A polymer forming a sensor 940 of the type described above is deposited on contact 915 (or noble metal coating 935 if provided). In the combinatorial approach to making sensors devices, thousands of sensors 940 might be made by varying the composition of two, three, four, or more different types of polymers. A flat surface for this purpose would be desirable.

If for some reason a sensor well becomes necessary to physically separate individual sensors, beyond the electrical separation offered by the addressable contacts 930, then a second insulator layer 950 may be provided with opening for sensors 940. Insulator layer 950 is preferably Teflon® (a trademark of E.I. DuPont de Nemours and Company), Teflon®-like material, or other fluoropolymer, although other insulators may be used. In the case that postprocessing is needed, a flat topography on integrated circuit 900 from the planarization step is highly desirable.

Particularly in the case of an integrated circuit, a premium is placed on the amount of real estate taken up by sensors 940. To conserve real estate area, it is desirable to place the sensors above semiconductor devices 905 that make up the electronics for the array. This effectively doubles the use of the real estate. Because of their size, sensors 940 can become the determinant of the size of the chip if each sensor 940 has to be isolated physically from every other sensor 940. In this case, the dilution of the solution used to cast sensor 940 is desired to be as high as possible. The thinner the film the finer the degree to which it can be patterned or physically localized by other means.

In a preferred embodiment of integrated circuit 900, sensor 940 should be as thin as possible without destroying its electrical properties. If the desired thickness of the polymer film becomes smaller than the conductive particle size, solution casting becomes impractical. Thus, in an alternate embodiment of the present invention, sensors 940 are formed by putting the conductive particles down and then coating the conductive particles with the polymer films through a vapor deposition process. In some embodiments, these films may be made with no polymer at all, and yet still be sensitive to analytes. By putting down the conductive particles first and then coating them with a thin film of polymer, one could have an effective active film arbitrarily thin supported by the larger conductive particles in a porous configuration. Put another way, instead of casting a polymer film with included conductive particles, sensor 940 is formed by making a porous particle film with polymer coating the particles. This improves the response much faster and the lateral dimensions determined by the localization of a polymer vapor deposition.

Another response time enhancement is to make sensor 940 with an inert or sacrificial particle filler which is either very permeable or removable after deposition. While this does not change the thickness parameter positively, in some cases it is a simpler way to achieve the response time benefits of the spongy film detailed above with the application techniques that are in use today.

Figure 10:
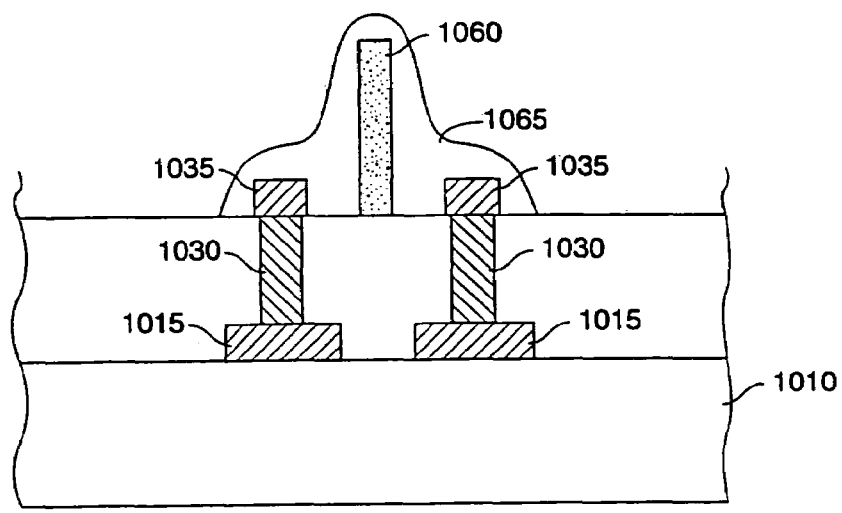
FIG. 10 shows a cross section of another embodiment of a sensor site.

FIG. 10 is a cross-sectional diagram showing another example of a sensor element of the present invention created by another method. This technique also benefits from the planarized integrated circuit described with respect to FIG. 9. In this embodiment, semiconductor devices 1005, conductors 1010, and contacts 1030 are formed and the integrated circuit is planarized as described above, and optional noble metal coating 1035 is formed above contact 1030. Then, micromachining techniques are used to form high, hurdle-like structures 1060. By this technique, it is possible to place contacts 1030 very close together on the surface of the integrated circuit. A polymer film 1065 is deposited onto hurdle-like structure 1060 with a thickness that may be determined by the surface tension or wetting properties of the polymer, solvent conductive particle mixture, rather than the volume in the drop or dispensed amount. This allows the sensor to be thinner, the response faster and the silicon area to be reduced.

Figure 11:
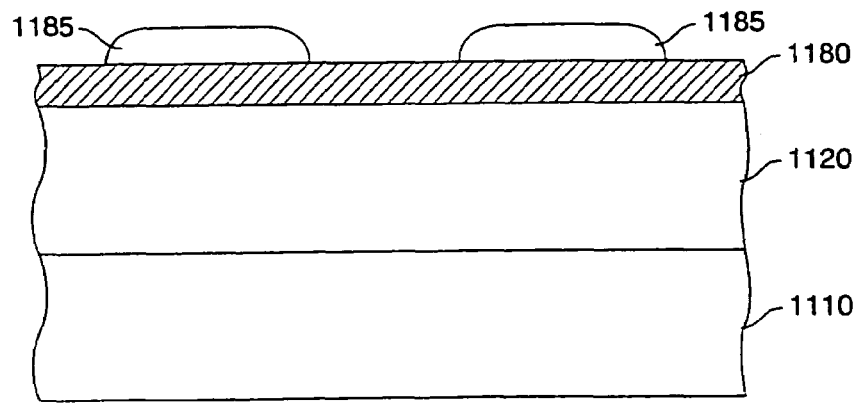
FIG. 11 shows a cross section of a further embodiment of a sensor site.

FIG. 11 shows another embodiment of the present invention that may take advantage of the planarization technique described above with respect to FIG. 9. Above the planarized insulator layer 1120, a very high impedance film 1180 is placed across semiconductor devices (not shown in FIG. 11) that form the array. Chemisensitive sensors 1185 are deposited right on top of high impedance film 1180 forming a distributed parallel resistor. This allows working in a domain of thinness where the actual signal generating these film does not need to be continuous. Even if short segments change, the terminal resistances within the array would be impacted.

Figure 12:
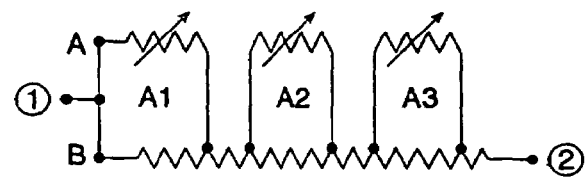
FIG. 12 shows an equivalent circuit diagram for the case of a discontinuous film on top of a continuous high-impedance film.

In particular, the equivalent circuit for the case of a discontinuous film on top of a continuous high-impedance film is shown in FIG. 12. The high impedance film is represented by leg E in the drawing or as a continuous resistor. Leg A of the drawing shows a group of variable resistors that are in parallel with the underlying resistor. When the resistors A1 through A3 change in response to the presence of an analyte, the resistance between points 1 and 2 of the drawing change even though the changing film may not be continuous.

Figure 13:
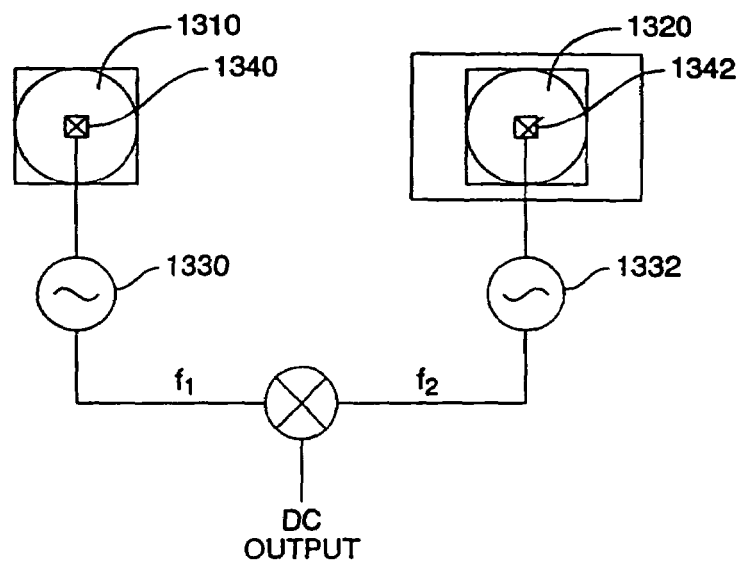
FIG. 13 is a block diagram of a technique for evaluating or measuring the capacitance of a sensor to detect an analyte.

FIG. 13 is a block diagram of an embodiment of the present invention that measures a capacitance of the sensor material to determine the presence of an analyte. While FIG. 13 shows only a single pair of sensors, the circuitry may also be expanded to include an array of sensors or an array of pairs of sensors. Each sensor in the array may include a different type of sensor material from other sensors as described above.

Capacitance may be measured in a variety of ways. FIG. 13 depicts one such method. However, other circuitry for measuring capacitance may be substituted for the circuitry shown. In the embodiment shown, two sensors 1310 and 1320 are provided. Sensors 1310 and 1320 are sensors formed substantially identical to one another. However, sensor 1410 is exposed such that analytes may penetrate the sensor material and cause it to expand. On the other hand, sensor 1320 is covered by an insulator layer so that it will not be affected by analytes. As such, sensor 1320 is a reference sensor, and its capacitance can be compared with the capacitance of sensor 1310 to determine if sensor 1320 has expanded due to the presence of an analyte.

One technique of evaluating the capacitors of the sensors involves frequency generators. Frequency generators 1330 and 1332 are coupled to sensors 1310 and 1320, respectively, through contacts 1340 and 1342. Frequency generators 1330 and 1332 output an oscillating signal at a particular frequency, and receive back return signals f1 and f2. Return signals f1 and f2 may be phase-shifted or frequency shifted, depending upon the capacitance of the sensor. Thus, if sensor 1310 has not expanded, the capacitance is the same as that of sensor 1320 and f1 is the same as f2. In the case when an analyte is present, the capacitance of sensor 1320 is greater, and thus f1 is not the same as f2. In fact, the difference between f1 and f2 may be used to determine the change in capacitance.

The return signals f1 and f2 are input to a discriminator mixer 1350. Discriminator mixers are well known in the electrical arts, and in particular for example, in the design of phase locked loops. Mixer 1350 receives two frequencies, and outputs a DC output that is zero if the frequencies are the same, and nonzero if the frequencies are different. The greater the frequency difference, the higher the value of the DC output. Thus, if the output of mixer 1350 is zero, then the capacitance of the two sensors are the same, and no analyte is present; if the magnitude of the output is nonzero, then an analyte is present, and may be identified by the value of the DC output.

Of course, other capacitance measuring circuitry may also be used. For example, two similar adjacent sensors may be formed such that they have room to expand in a sideways direction. Each of the two sensors are coupled to a different conductive trace, and the sensors are coupled through the conductive trace to a capacitance measuring circuit. When no analyte is present, the sensors have a certain separation, that is known, and thus has a known capacitance. When an analyte is present, the sensors expand and the distance between them shortens causing the capacitance to change. By measuring the change in capacitance, the presence of the analyte may be determined.

Figure 14:
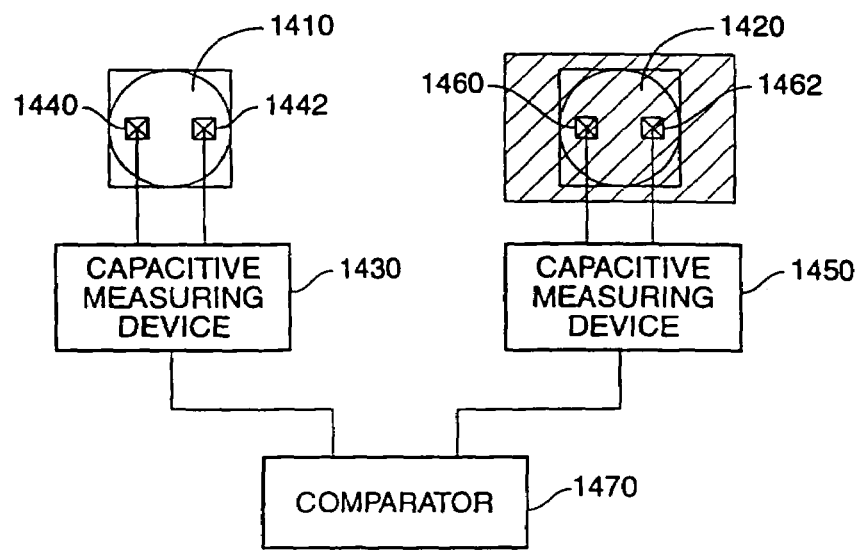
FIG. 14 shows another embodiment for evaluating or measuring the capacitance of a sensor element.

FIG. 14 shows another embodiment of the present invention for measuring the capacitance of a sensor element. Two similar sensors 1410 and 1420 are provided. In a specific embodiment, sensors 1410 and 1420 are substantially identical. A capacitive measuring device 1430 coupled to sensor 1410 by two conductors 1440 and 1442 through contacts or otherwise. The capacitive measuring device is any device capable of determining a capacitance of sensor 1410. Similarly, a second capacitance measuring device is coupled to sensor 1420 through two conductors 1460 and 1462. Sensor 1420 is isolated from exposure to analytes, while sensor 1410 may be exposed to them. A comparator 1470 compares the capacitances measured from the two sensors 1410 and 1420. These values may be analyzed by various techniques described above or otherwise.

Figure 15:
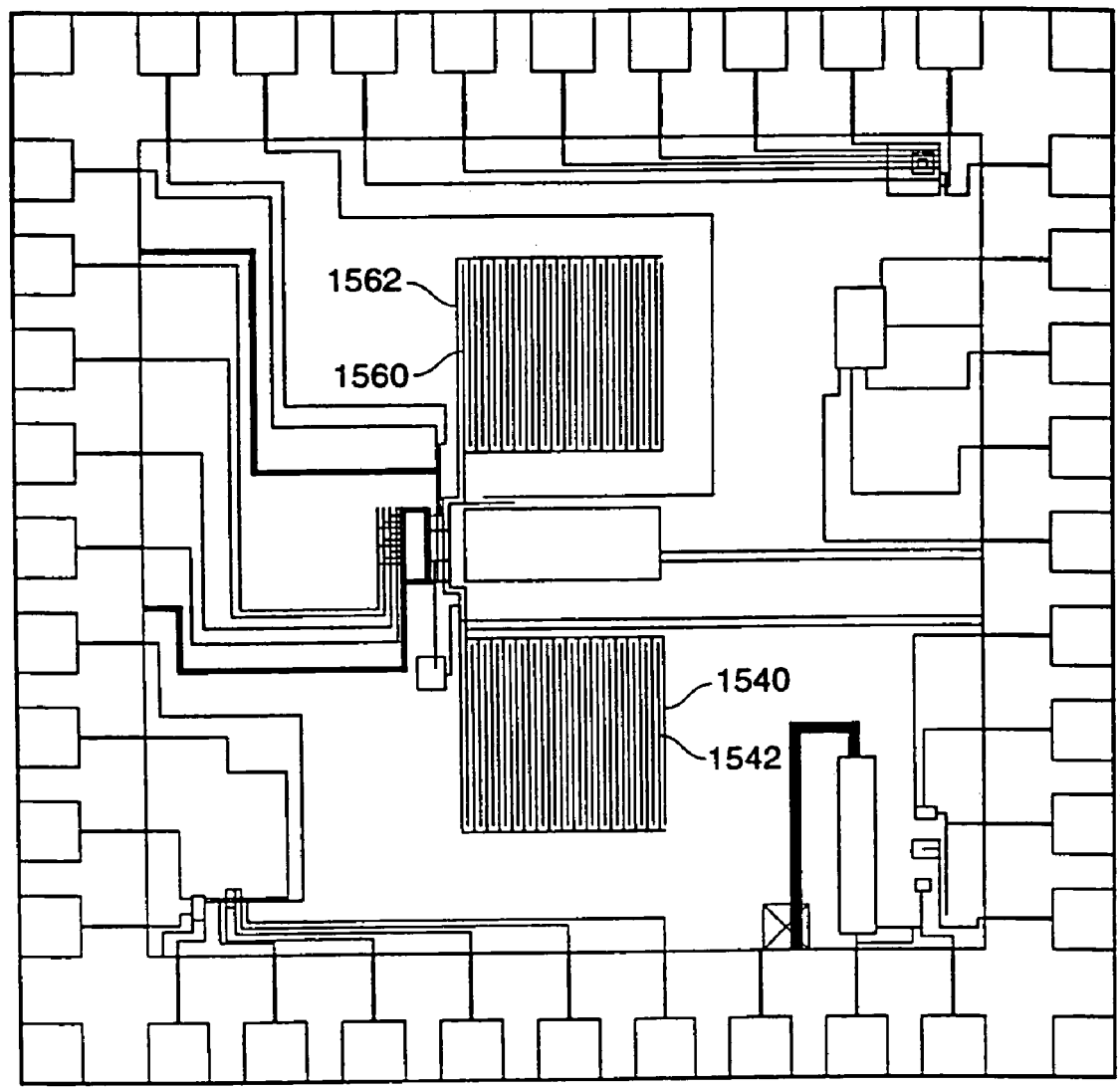
FIG. 15 shows a layout of capacitive sensor sites for an integrated circuit.

FIG. 15 shows an integrated circuit layout that may be used for the circuit shown in FIG. 14. Conductors 1540 and 1542 are interdigitated on the integrated circuit. These conductors are associated with one capacitor. Sensor 1510 is formed above the interdigitated conductors. Similarly, sensor 1520 is formed above interdigitated conductors 1560 and 1562. These conductors are associated with another capacitor.

Figure 16:
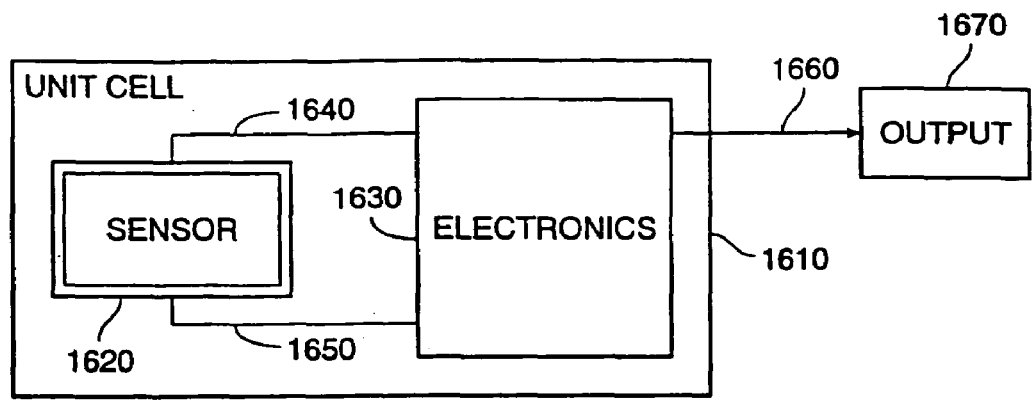
FIG. 16 shows a unit cell.

FIG. 16 shows a "unit cell" 1610 for a sensor of the analyte detection chip of the present invention. To form a plurality of sensors, unit cell 1610 may be repeated as many times as desired. For example, for an analyte detection chip with ten sensors, the unit cell is repeated ten times. For an analyte detection chip with thirty sensors, the unit cell is repeated thirty times. For a chip with 100 sensors, the unit cell is repeated 100 times. For a chip with "n" sensors, the unit cell is repeated at least "n" times.

As discussed above, a basic embodiment of unit cell 1610 includes sensor 1620 by itself. Electrical connections from the unit cell will be connected to other electronic circuitry, on-chip or off-chip, for further processing. For example, in a two-chip analyte detection chipset solution, a first of the chips may contain a plurality of sensors 1620 and their respective electrical connections. A second of the chips may be electrically coupled to sensors 1620 to process the signals from the sensors on the first chip.

A more highly integrated embodiment of unit cell 1610 includes sensor 1620 and electronics 1630, both on the same chip or substrate. Electronics 1530 may be formed beneath the sensor site of sensor 1620, as was described for FIG. 4 above. Electronics 1630 are electrically coupled to sensor 1620 by connections 1640 and 1650. Electronics 1630 processes the signals from the sensor. The processing includes amplification or filtering, or both. An output 1660 of the electronics may be coupled to other circuitry 1670 for even further processing. For example, the other circuitry may be off-chip for classifying the analyte.

Figure 17:
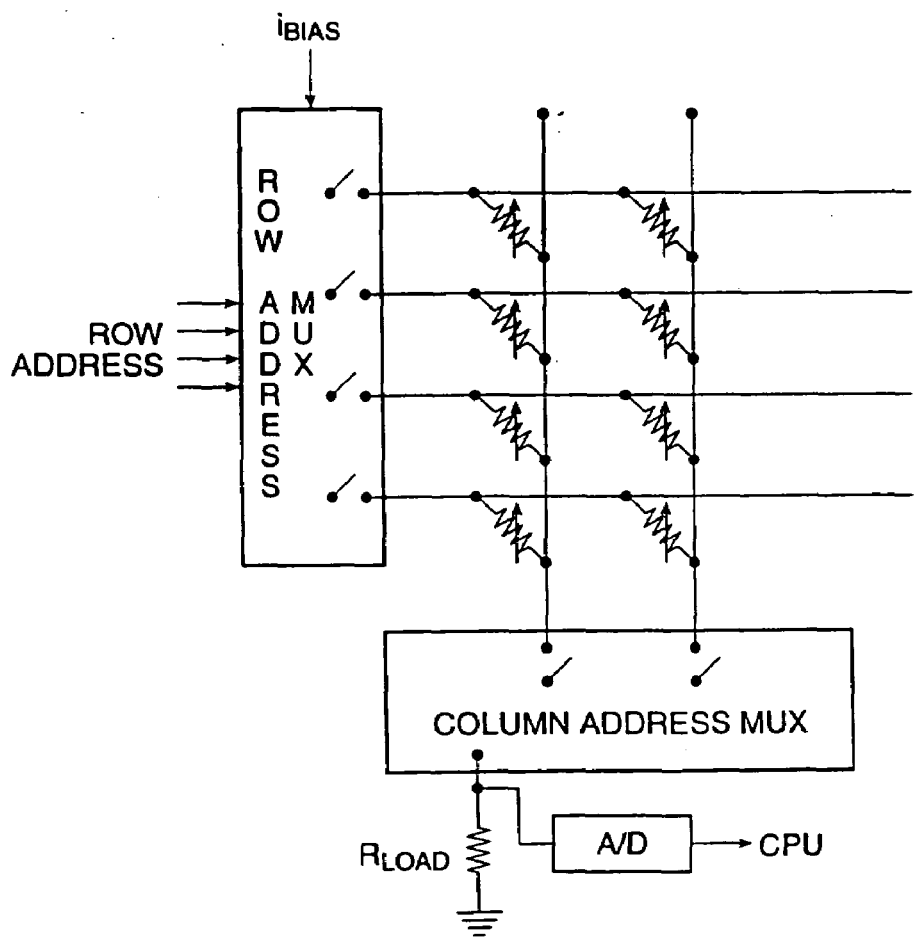
FIG. 17 shows a diagram of circuitry for reading out data from an array of sensors.

FIG. 17 shows an embodiment of circuitry for reading out a sensor array. As the number of wires grows with the number of sensors in an array, the practicality of using an inactive array is reduced. It becomes desirable as the number of sensors in the array approaches about 100 to reduce the wiring complexity with the addition of a matrix addressing scheme shown in FIG. 17. The array of chemically sensitive sensors is shown in this embodiment as variable resistors, each connected between a row bias line and a column read line. A row and a column multiplexer are to "sample" the sensor data in a scheme somewhat like to scanning a television picture. A row address is translated into the application of bias (i. e., iBias) to one row, and the column address is translated into the closure of a column read switch switching the output to a load resistor that is at the input of an analog-to-digital (A/D) converter whose output is in turn fed to the controller of the system. It should be clear that the functions of bias and read could be reversed and that other configurations of lead resistors, included buffering circuitry and many other functions could be included.

In an embodiment of an array of sensor cells, there may also be dummy rows and columns of sensors, which is a row or column of sensors is formed but not used functionally as are active rows and columns of sensors. For example, at row and column edges of the array, dummy rows and columns of sensors may be formed. These dummy rows and columns of sensors may be used to ensure the active interior row and columns of sensors are relatively uniform, since sensors at the edge may exhibit some edge effects by not having a similar number of adjacent sensors as for the interior sensors.

Dummy rows and columns (not necessarily at edges of the array) may also be used in a redundancy scheme when these are activated, possibly by laser programming or programming of nonvolatile or one-time programmable memory elements such as Flash, EEPROM, EPROM, or antifuse cells. These dummy row and columns may be used in the place of other rows and columns that are or have become defective. For example, a redundancy scheme may help improve the yield of good die, or increase the service life of an analyte detection chip.

Figure 18:
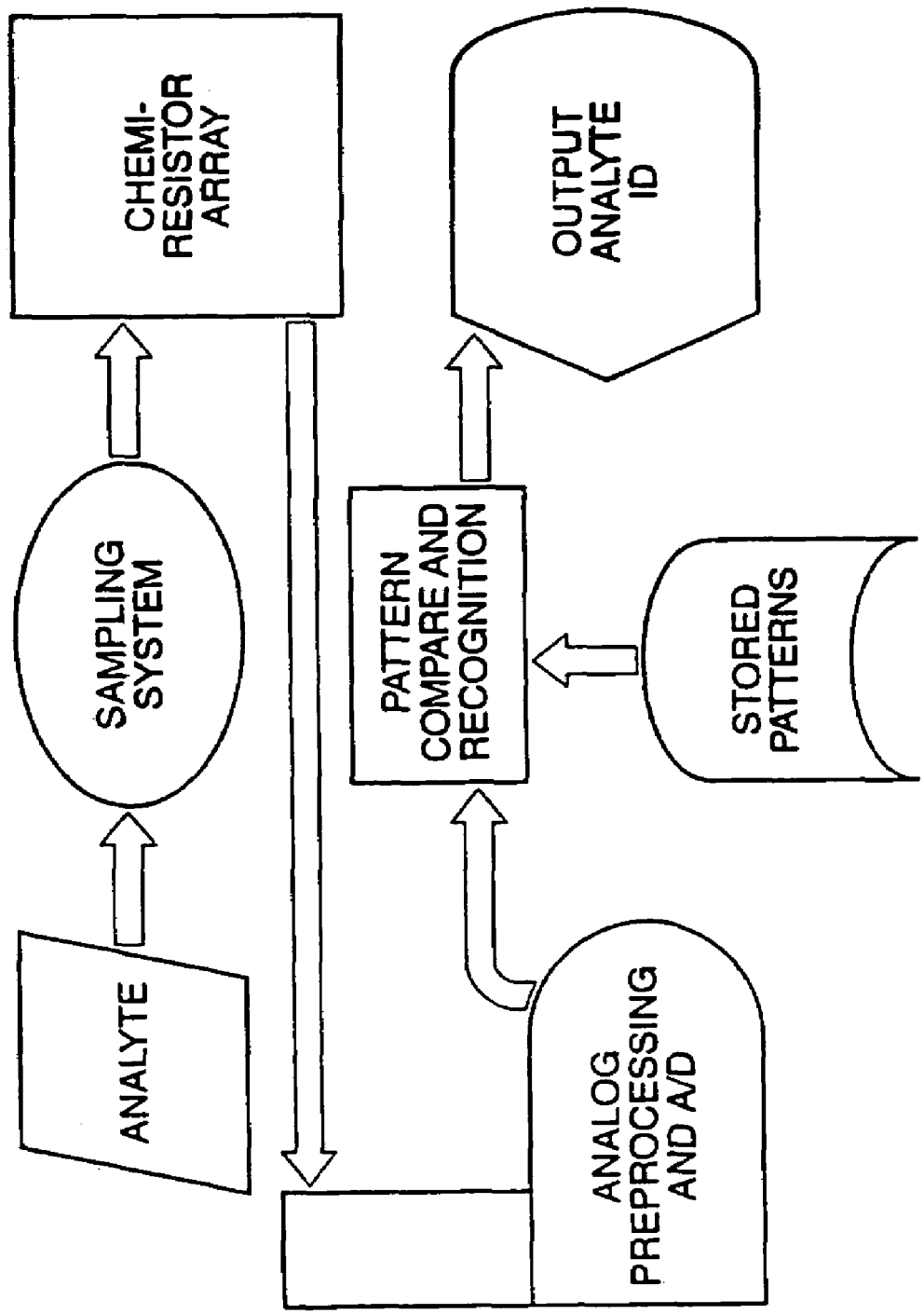
FIG. 18 shows a diagram of an analyte detection system.

FIG. 18 shows a block diagram of an analyte detection system. The block diagram for a discrete system that has been developed are shown in the analyte detection system block diagram and system design. Any full analyte sampling system should include a means for sampling the analyte of interest. This could be as simple as a stick to attach the sensors and a means for holding it in the vicinity of a vapor of interest, or as complex as a network of pumps and valves sequencing through a complex sampling routine. Once the analyte has been presented to the array of chemically sensitive transducers, the signals are processed and presented to an A/D converter. The pattern of response across the array is then compared to a stored pattern of response and an identification can be made through any number of possible input output channels as simple as wires to a control system or as complex as a visual display system.

Figure 19:
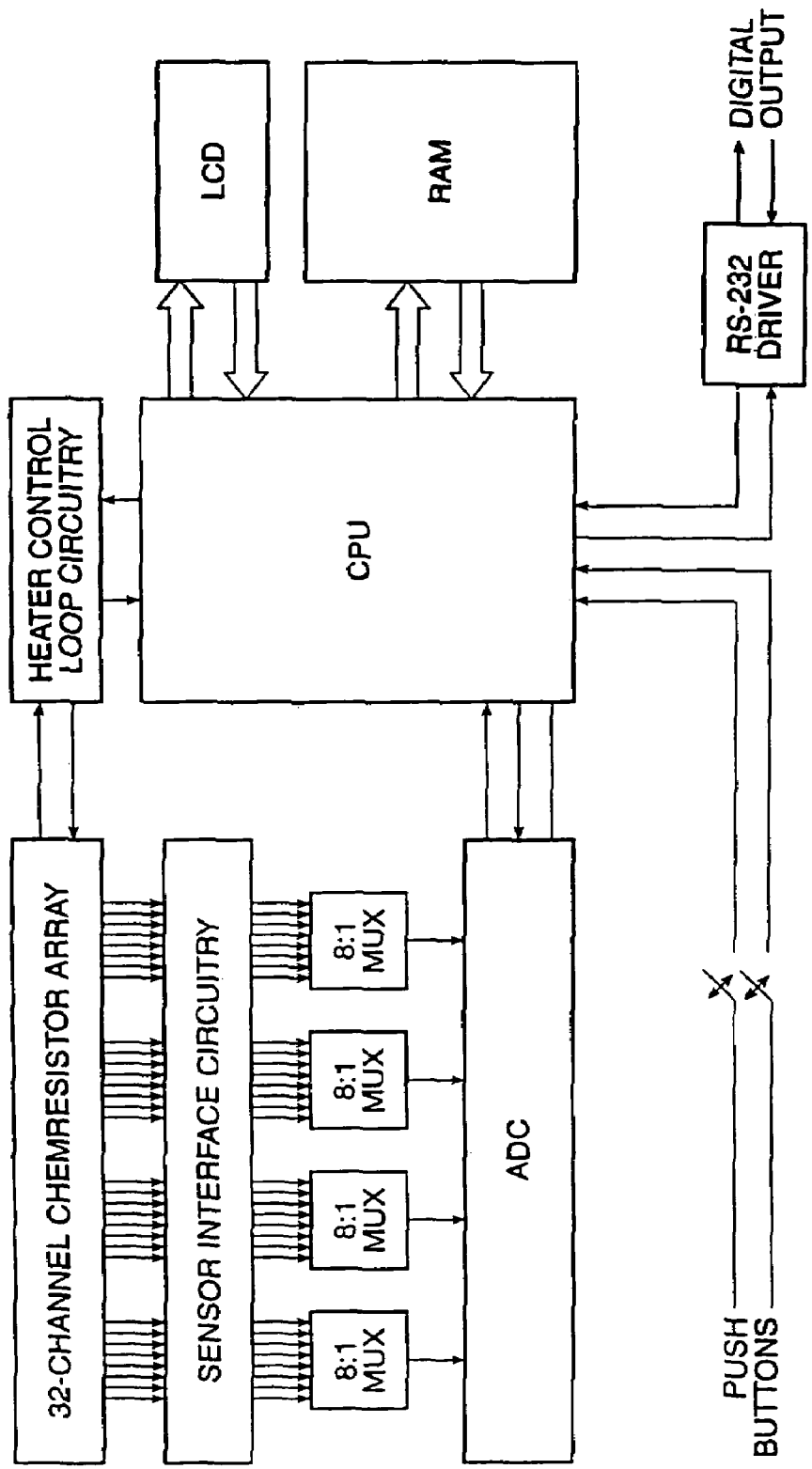
FIG. 19 shows a specific embodiment of an analyte detection system.

FIG. 19 shows a block diagram of a specific embodiment of an analyte system of the present invention. A particular embodiment of such a system is shown in the block diagram of a system that has been implemented in a discrete design. There are thirty-two sensors (e.g., chemiresistive sensors) organized in four groups of eight. The signals are buffered, and each bank of eight sensor signals is then fed through an 8-to-1 analog multiplexer to an A/D that has an additional 4-to-1 multiplexer internal to it. The data is streamed out of the A/D converter in a serial bit stream to a central processing unit (CPU). The CPU may be a computer. The CPU additionally is interfaced to a heater control system. As the chemically sensitive sensors are also temperature dependant, controlling the temperature in the system eliminates one source of noise. The data is stored by the CPU in random access memory (RAM) or in another storage media such as magnetic disk. The measurements can be compared to a learned pattern of response previously stored and the CPU can calculate the best match and report the result through the LCD panel display.

As the number of sensors grows beyond thirty-two, the number of connections can become impractical to make with solder or other physical attachment processes. More of the block diagram will then be integrated onto a chip since the wiring connections inside and integrated circuit are very reliable. As the number of sensors approaches 100, it makes economic sense to integrate a matrix measurement scheme on the same substrate as the sensors. As the number of sensors grows even further, the A/D converter can become overtaxed and more than one makes sense to keep the system throughput in the range of one second where the flow system time constant becomes the limitation to overall system response. As the number of sensors grows to an even larger number, the A/D technology needs to be changed to either a large array of slower A/Ds or a faster variety of converter or both. With an array of A/D converters on the chip a digital multiplexer needs to be added to funnel the outputs through to the CPU. As the number of sensor elements climbs to the millions, some condensation of the data needs to take place within the array itself.

The foregoing description of preferred embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize and practice the invention in various embodiments and with various modifications as are suited to the particular use contemplated. It is intended that the scope of the invention be defined by the following claims.

What is claimed is:

1. A method of fabricating a sensing device comprising:
   providing a semiconductor substrate having a conductor on the substrate;
   forming a contact to the conductor;
   forming a first insulating layer on an integrated circuit device that comprises the semiconductor substrate having the contact to the conductor formed thereon;
   planarizing the integrated circuit device exposing the contact, to thereby form a planarized integrated circuit device; and
   depositing a sensing material on the planarized integrated circuit device, wherein the sensing material is in electrical contact with the contact,
   wherein the depositing further comprises:
      depositing conductive particles on the planarized integrated circuit device; and
      covering the conductive particles with a nonconductive organic material.

2. The method of claim 1 further comprising covering the contact with a noble metal coating.

3. The method of claim 1 wherein the contact comprises tungsten.

4. The method of claim 1 wherein the covering comprises performing a vapor deposition on the integrated circuit device.

5. A method of fabricating a sensing device comprising:
   providing a semiconductor substrate having a conductor on the substrate;
   forming a contact to the conductor;
   forming a first insulating layer on an integrated circuit device that comprises the semiconductor substrate having the contact to the conductor formed thereon;
   planarizing the integrated circuit device exposing the contact, to thereby form a planarized integrated circuit device; and
   depositing a sensing material on the planarized integrated circuit device, wherein the sensing material is in electrical contact with the contact,
   wherein the sensing material comprises a sacrificial particle filler.

6. The method of claim 5 further comprising removing the sacrificial particle filler after deposition of the sensing material.

* * * * *